United States Patent [19]

Steiner et al.

[11] Patent Number: 5,068,371
[45] Date of Patent: Nov. 26, 1991

[54] NITROGEN-CONTAINING TITANOCENES, AND THE USE THEREOF

[75] Inventors: Eginhard Steiner, Füllinsdorf; Harry Beyeler, Basel; Rinaldo Hüsler, Wünnewil, all of Switzerland

[73] Assignee: Ciba-Geigy Corporation, Ardsley, N.Y.

[21] Appl. No.: 527,989

[22] Filed: May 23, 1990

[30] Foreign Application Priority Data

Jun. 1, 1989 [CH] Switzerland .................. 2075/89

[51] Int. Cl.$^5$ .............. C07F 7/28; G03C 1/68
[52] U.S. Cl. ............................ 556/53; 556/52; 556/9; 430/281; 430/288; 430/919; 430/920; 430/921; 430/922; 544/64; 544/225; 544/164; 544/165
[58] Field of Search .................. 556/53, 68, 11, 9; 502/152, 153, 155; 430/281, 325, 288, 919, 920, 921, 922; 544/64, 225, 164, 165

[56] References Cited

U.S. PATENT DOCUMENTS

| | | | |
|---|---|---|---|
| 4,590,287 | 5/1986 | Riediker et al. | 556/53 |
| 4,713,401 | 12/1987 | Riediker et al. | 556/68 |
| 4,857,654 | 8/1989 | Riediker et al. | 556/53 |
| 4,910,121 | 3/1990 | Riediker et al. | 556/53 X |
| 4,960,746 | 10/1990 | Hüsler et al. | 502/153 |
| 4,973,722 | 11/1990 | Doggweiler et al. | 556/53 X |

FOREIGN PATENT DOCUMENTS

| | | |
|---|---|---|
| 256981 | 2/1988 | European Pat. Off. |
| 318893 | 6/1989 | European Pat. Off. |
| 318894 | 6/1989 | European Pat. Off. |

OTHER PUBLICATIONS

M. A. Chaudhari, et al., J. Organomet. Chem., 2, 206(1964).
C. Tamborski et al., J. Organomet. Chem., 4, 446 (1965).

*Primary Examiner*—Arthur C. Prescott
*Attorney, Agent, or Firm*—Luther A. R. Hall

[57] ABSTRACT

Titanocenes of the formula I

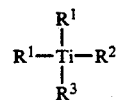

in which $R^1$ are cyclopentadienyl$^\ominus$ groups and $R^2$ and $R^3$ are aromatic radicals which are substituted in both ortho-positions by fluorine and, in addition, are substituted by a pyrrylalkyl group, amidoalkyl group or imidoalkyl group, are suitable as photoinitiators for the photopolymerization of ethylenically unsaturated compounds.

16 Claims, No Drawings

NITROGEN-CONTAINING TITANOCENES, AND THE USE THEREOF

The present invention relates to titanocenes containing fluoroaryl radicals which are substituted by pyrrylalkyl groups or amidoalkyl groups, to a process for the preparation thereof and to the use thereof as photoinitiators for the photopolymerization of ethylenically unsaturated compounds.

U.S. Pat. No. 4,590,287 discloses that titanocenes containing fluoroaryl ligands are excellent photoinitiators. The fluoroaryl radicals of these titanocenes may carry further substituents, including amino groups and aminoalkyl groups. U.S. Pat. No. 4,857,654 discloses titanocenes having polyoxaalkylene chains on the fluoroaryl ligands. EP-A-256,981 describes titanocenes containing silylated cyclopentadienyl radicals. EP-A-318,894 discloses titanocenes having pyrrole substituents on the fluoroaryl ligands, EP-A-318,893 describes titanocenes having nitrogen-containing ligands on the fluoroaryl radical, U.S. Pat. No. 4,713,401 discloses titanocenes which have $CF_3$ substituents in place of fluorine atoms on the aryl ligands. Titanocenes containing fluoroaryl radicals which are substituted by pyrrylalkyl groups, amidoalkyl groups or imidoalkyl groups have hitherto not been disclosed. However, it has been shown that titanocenes substituted in this manner are likewise excellent photoinitiators.

The invention relates to titanocenes of the formula I

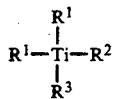

in which both the $R^1$ radicals, independently of one another, are cyclopentadienyl$^\ominus$, indenyl$^\ominus$ or 4,5,6,7-tetrahydroindenyl$^\ominus$, each of which is unsubstituted, monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{16}$aryl, $C_7$-$C_{16}$aralkyl, -Si($R^4$)$_3$, -Ge($R^4$)$_3$, cyano or halogen, and $R^4$ is $C_1$-$C_{12}$alkyl, $C_5$-$C_{12}$cycloalkyl, $C_6$-$C_{10}$aryl or $C_7$-$C_{16}$aralkyl, $R^2$ is a 6-membered carbocyclic or 5- or 6-membered heterocyclic aromatic ring which is substituted by fluorine atoms at least in the two ortho-positions to the titanium-carbon bond, and in which the aromatic ring may contain further substituents, and $R^3$, independently, is as defined for $R^2$, $R^2$ and $R^3$ in the titanocenes being substituted by a radical of the formula II, IIa or IIb

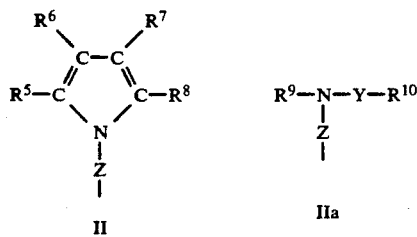

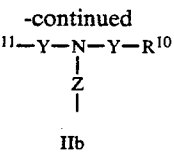

in which $R^5$, $R^6$, $R^7$ and $R^8$, independently of one another, are hydrogen or linear or branched $C_1$-$C_{18}$alkyl, $C_2$-$C_5$alkenyl, $C_7$-$C_9$aralkyl, $C_7$-$C_9$alkaryl, $C_8$-$C_{10}$alkaralkyl, $C_6$-$C_{10}$aryl, 2-furyl, $C_5$-$C_8$cycloalkyl, $C_5$-$C_8$cycloalkenyl, $C_2$-$C_{12}$alkanoyl, $C_2$-$C_{12}$alkoxycarbonyl, —CHO, —Si($R^4$)$_3$ or —Ge($R^4$)$_3$, these radicals being unsubstituted or substituted by $C_2$-$C_8$dialkylamino, bis[2-($C_1$-$C_4$alkoxy)ethyl]amino, morpholino, piperidino, N-methylpiperazino, pyrrolidino, quaternary $C_3$-$C_{10}$trialkylammonium, $C_1$-$C_{12}$alkoxy, —(—OCH$_2$CH$_2$—)$_p$—O—$C_1$-$C_{16}$alkyl, in which p is a number from 1 to 20, 1,3-dioxolan-2-yl, 4-methyl-1,3-dioxolan-2-yl, —OCH$_2$CH$_2$O—, $C_2$-$C_{12}$alkoxycarbonyl, $C_2$-$C_{12}$alkanoyloxy, $C_2$-$C_{12}$alkanoyl, $C_1$-$C_{12}$alkylthio, halogen, cyano or —Si($R^4$)$_3$, or $R^5$ and $R^6$ and/or $R^7$ and $R^8$ or $R^6$ and $R^7$ are each together —(CH$_2$)$_3$—, —(CH$_2$)$_4$—, —CH=CH—CH=CH—, —CH=CH—C($R^{12}$)=CH—, —CH$_2$OCH$_2$— or —CH$_2$N(-$C_1$-$C_4$alkyl)CH$_2$—, in which $R^{12}$ is hydroxyl, $C_1$-$C_4$alkoxy or $C_2$-$C_4$alkanoyloxy, Y is a —CO—, —CS—, —COO—, —SO$_2$— or —Si($R^4$)$_2$— group, $R_9$ is hydrogen, linear or branched $C_1$-$C_{20}$alkyl, $C_2$-$C_{20}$alkenyl, $C_3$-$C_8$cycloalkyl, $C_4$-$C_{20}$cycloalkylalkyl, $C_4$-$C_{20}$alkylcycloalkyl, $C_5$-$C_{20}$alkylcycloalkylalkyl, $C_6$-$C_{20}$cycloalkenylalkyl, $C_6$-$C_{14}$aryl, $C_7$-$C_{20}$aralkyl, $C_7$-$C_{20}$alkaryl, $C_8$-$C_{20}$alkaralkyl or $C_3$-$C_{12}$trialkylsilyl, these radicals being unsubstituted or substituted by $C_1$-$C_{18}$alkoxy, $C_1$-$C_{18}$alkylthio, $C_1$-$C_{18}$alkylsulfonyl, $C_6$-$C_{10}$arylsulfonyl, $C_7$-$C_{20}$alkarylsulfonyl, 2-tetrahydrofuranyl or cyano, $R^{10}$ has one of the meanings given for $R^9$, or is $C_1$-$C_{20}$haloalkyl, $C_2$-$C_{20}$alkyl which is interrupted by —CO—, or is $C_1$-$C_{12}$alkyl which is substituted by —COOH or —COOR$^4$, and in the case where Y is —CO—, —CS— or —SO$_2$—, may alternatively be —NR$^{13}$R$^{14}$ in which $R^{13}$ and $R^{14}$, independently of one another, have one of the meanings given for $R^9$, or $R^{13}$ and $R^{14}$ together are $C_3$-$C_7$alkylene which may be interrupted by —O—, —S— or —N($R^{15}$)—, in which $R^{15}$ is hydrogen, $C_1$-$C_{12}$alkyl, $C_3$-$C_{12}$alkenyl, $C_7$-$C_{12}$aralkyl or $C_2$-$C_{20}$alkanoyl, or $R^9$ and $R^{10}$ together are linear or branched $C_2$-$C_8$alkylene or $C_2$-$C_8$alkylene which is substituted by halogen, $C_1$-$C_4$alkoxy, allyloxy or —NR$^{13}$R$^{14}$, or are a divalent radical of the formula

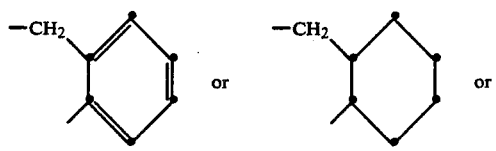

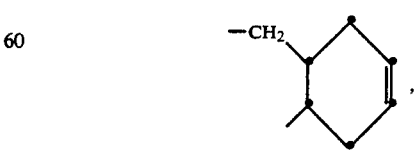

$R^{11}$ has one of the meanings given for $R^{10}$, or $R^{11}$ and $R^{10}$ together are $C_1$-$C_8$alkanediyl, $C_2$-$C_8$alkenediyl, $C_6$-$C_{14}$arenediyl, $C_4$-$C_{12}$cycloalkanediyl, $C_5$-$C_{12}$cycloalkenediyl, $C_6$-$C_{14}$cycloalkadienediyl, $C_7$-$C_{20}$bicycloalkanediyl, $C_7$-$C_{20}$bicycloalkenediyl, or $C_2$-$C_4$alkanediyl which is interrupted by —O—, —S— or —N($R^{15}$)—, these radicals being unsubstituted or substituted by one or more of the substituents halogen, $C_1$-$C_{10}$alkoxy, $C_1$-$C_{20}$alkyl, $C_3$-$C_{20}$alkenyl or $C_6$-$C_{14}$aryl, and Z is $C_1$-$C_{20}$alkanediyl which is unsubstituted or substituted by —COO$R^4$, —CN or halogen.

The $R^1$ groups are preferably identical radicals. Suitable substituents for $R^1$ are: linear or branched alkyl or alkoxy having 1 to 18, particularly 1 to 12 and in particular 1 to 6, C atoms, and alkenyl having 2 to 18, particularly 2 to 12, and in particular 2 to 6, C atoms, for example methyl, ethyl, propyl, isopropyl, n-butyl, tert.-butyl, pentyl, hexyl, octyl, decyl, dodecyl, tetradecyl, hexadecyl, octadecyl and corresponding alkenyl and alkoxy groups; cycloalkyl having 5 to 8 ring carbon atoms, for example cyclopentyl, cyclohexyl, cycloheptyl, methylcyclopentyl and methylcyclohexyl; aryl having 6 to 10 C atoms and aralkyl having 7 to 16 C atoms, for example phenyl, naphthyl, benzyl and phenylethyl; cyano and halogen, particularly F, Cl and Br; —Si($R^4$)$_3$ or —Ge($R^4$)$_3$, in which $R^4$ is preferably $C_1$-$C_8$alkyl, cyclohexyl, phenyl or benzyl. Examples of alkyl $R^4$ are methyl, ethyl, n- and i-propyl, n-, i- and t-butyl, pentyl, hexyl, heptyl and octyl.

The radicals $R^1$ may contain up to 5, but particularly up to 3 substituents. Both $R^1$ groups are preferably cyclopentadienyl$^\ominus$ or methylcyclopentadienyl$^\ominus$ radicals, in particular cyclopentadienyl$^\ominus$ radicals.

$R^2$ as a 6-membered carbocyclic, aromatic and fluorine-substituted ring may be fluorine-substituted indene, indane, fluorene, naphthalene and, particularly, phenyl. $R^2$ as a heterocyclic, aromatic and 5-membered radical preferably contains one hetero atom and as a 6-membered ring preferably contains 1 or 2 hetero atoms. Preferably, both ortho-positions are substituted by fluorine. Examples are 4,6-difluoroinden-5-yl, 5,7-difluoroindan-6-yl, 2,4-difluorofluoren-3-yl, 1,3-difluoronaphth-2-yl, 2,6-difluorophen-1-yl, 2,4-difluoropyrr-3-yl, 2,4-difluorofur-3-yl, 2,4-difluorothien-3-yl, 2,4-difluoropyrid-3-yl, 4,6-difluoropyrimidin-5-yl and 3,5-difluoropyridazin-4-yl.

In a preferred embodiment, $R^2$ in the formula I is substituted 2,6-difluorophen-1-yl. In particular, $R^2$ is 2,6-difluorophen-1-yl which contains 1 to 3 further substituents, of which at least one is a radical of the formula II, IIa or IIb.

$R^3$ preferably has the same meaning as $R^2$.

In a preferred embodiment, $R^2$ and $R^3$ are 2,6-difluorophen-1-yl to which a radical of the formula II, IIa, or IIb is bonded, and which may contain a further 1 or 2 identical or different substituents.

A preferred group of titanocenes of the formula I is formed by those in which both $R^1$ groups are cyclopentadienyl$^\ominus$, and $R^2$ and $R^3$ are radicals of the formula III

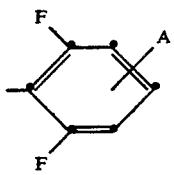

III in which A is a group of the formula II, IIa or IIb, in particular those in which A is a group of the formula II.

In formula III, the group A is preferably bonded in the ortho-position to an F atom.

Examples of substituents on $R^5$, $R^6$, $R^7$ and $R^8$ are $C_2$-$C_8$dialkylamino, preferably $C_2$-$C_4$dialkylamino, for example dimethylamino, diethylamino, di-n-propylamino, di-n-butylamino or methylethylamino; bis[2-($C_1$-$C_4$alkoxy)ethyl]amino, for example bis(2-methoxyethyl)amino or bis(2-ethoxyethyl)amino; morpholino; piperidino; N-methylpiperazino; pyrrolidino; quaternary $C_3$-$C_{10}$trialkylammonium, preferably $C_3$-$C_6$trialkylammonium, for example trimethylammonium, triethylammonium, dimethylethylammonium or dimethylpropylammonium; $C_1$-$C_{12}$alkoxy, preferably $C_1$-$C_4$alkoxy, for example methoxy, ethoxy, propoxy and butoxy; $-(OCH_2CH_2)_p$O$C_1$-$C_{16}$alkyl, in which p is preferably a number from 1 to 3, for example $CH_3$-O-$(CH_2CH_2O)_2$; 1,3-dioxolan-2-yl; 4-methyl-1,3-dioxolan-2-yl, —OCH$_2$CH$_2$O—, $C_2$-$C_{12}$alkoxycarbonyl, preferably $C_2$-$C_6$alkoxycarbonyl, for example methoxycarbonyl, ethoxycarbonyl, propoxycarbonyl and butoxycarbonyl; $C_2$-$C_{12}$alkanoyloxy, preferably $C_2$-$C_6$alkanoyloxy, for example acetyloxy, propionyloxy and butyryloxy; $C_2$-$C_{12}$alkanoyl, preferably $C_2$-$C_6$alkanoyl, for example acetyl, propionyl and butyryl; $C_1$-$C_{12}$alkylthio, preferably $C_1$-$C_6$alkylthio, for example methylthio, ethylthio, propylthio and butylthio; halogen, preferably F, Cl and Br; cyano; -Si($R^4$)$_3$, in which $R^4$ is preferably $C_1$-$C_6$alkyl, for example butyl, propyl, ethyl and, particularly, methyl.

Alkyl $R^5$, $R^6$, $R^7$ and $R^8$ preferably contain 1 to 12 and particularly 1 to 8 C atoms. Examples are methyl, ethyl, and the isomers of propyl, butyl, pentyl, hexyl, heptyl, octyl, nonyl, decyl, undecyl, dodecyl, tridecyl, tetradecyl, hexadecyl and octadecyl. Alkenyl $R^5$, $R^6$, $R^7$ and $R^8$ preferably contain 2 to 4 C atoms. Examples are vinyl, allyl, crotonyl, 2-methylprop-1-en-1-yl, but-1-en-1-yl, but-2-en-2-yl, but-2-en-1-yl, but-3-en-1-yl or -2-yl, or pent-1-en-1-yl. Aryl $R^5$, $R^6$, $R^7$ and $R^8$ are in particular phenyl. Aralkyl or alkaryl $R^5$, $R^6$, $R^7$ and $R^8$ may be, for example, benzyl, phenylethyl, phenylpropyl, methylphenyl, ethylphenyl, propylphenyl, dimethylphenyl and methylethylphenyl. Alkaralkyl $R^5$, $R^6$, $R^7$ and $R^8$ may be, for example, methylbenzyl, ethylbenzyl, propylbenzyl, (methylphenyl)ethyl or dimethylbenzyl. Cycloalkyl and cycloalkenyl $R^5$, $R^6$, $R^7$ and $R^8$ are particularly cyclopentyl, cyclopentenyl, cyclohexyl or cyclohexenyl. Alkanoyl $R^5$, $R^6$, $R^7$ and $R^8$ preferably contain 2 to 8, particularly 2 to 6, C atoms. Examples are acetyl, propionyl, butanoyl, pentanoyl, hexanoyl, octanoyl and dodecanoyl. $C_2$-$C_{12}$Alkoxycarbonyl $R^5$, $R^6$, $R^7$ and $R^8$ are, in particular, $C_2$-$C_5$alkoxycarbonyl, for example methoxycarbonyl, ethoxycarbonyl or butoxycarbonyl. $R^5$, $R^6$, $R^7$ and $R^8$ may be the —Ge($R^4$)$_3$ and preferably —Si($R^4$)$_3$ groups. In these groups, $R^4$ is preferably $C_1$-$C_{12}$alkyl, particularly $C_1$-$C_8$alkyl and in particular $C_1$-$C_4$alkyl. The —Si(CH$_3$)$_3$ group is particularly preferred.

In a preferred sub-group, $R^5$, $R^6$, $R^7$ and $R^8$, independently of one another, are hydrogen or unsubstituted or substituted $C_1$-$C_{12}$alkyl, $C_2$-$C_5$alkenyl, $C_7$-$C_9$phenylalkyl, $C_7$-$C_{10}$alkylphenyl, phenyl, 2-furyl, $C_5$- or $C_6$cycloalkyl, $C_5$- or $C_6$cycloalkenyl, $C_2$-$C_8$alkanoyl, $C_2$-$C_5$alkoxycarbonyl, —CHO or —Si($R^4$)$_3$, in which $R^4$ is $C_1$-$C_8$alkyl or phenyl.

In another preferred sub-group, $R^5$, $R^6$, $R^7$ and $R^8$, independently of one another, are a hydrogen atom, or unsubstituted or substituted $C_1$-$C_8$alkyl, $C_2$-$C_4$alkenyl, benzyl, phenyl, 2-furyl, $C_5$- or $C_6$cycloalkyl, $C_2$-$C_6$alkanoyl, $C_2$–$C_5$alkoxycarbonyl, —CHO or —Si($R^4$)$_3$, in which $R^4$ is $C_1$–$C_4$alkyl.

$R^9$ may be substituted by $C_1$–$C_{18}$alkoxy, $C_1$–$C_{18}$alkylthio and $C_1$–$C_{18}$alkylsulfonyl, which preferably contain 1 to 12, particularly 1 to 6 and in particular 1 to 4, C atoms. Examples of alkyl groups in these substituents are methyl, ethyl and the isomers of propyl, butyl, pentyl, hexyl, heptyl, octyl, nonyl, decyl, undecyl, dodecyl, tetradecyl, hexadecyl and octadecyl. Further substituents of $R^9$ are arylsulfonyl and alkarylsulfonyl, for example phenylsulfonyl, tolylsulfonyl or p-dodecylphenylsulfonyl.

$R^9$ may be linear or branched $C_1$–$C_{20}$alkyl, preferably $C_1$–$C_{12}$alkyl and particularly $C_1$–$C_8$alkyl. Examples are methyl, ethyl and the isomers of propyl, butyl, pentyl, hexyl, heptyl, octyl, nonyl, decyl, undecyl, dodecyl, tetradecyl, hexadecyl and octadecyl. $R^9$ may be $C_3$–$C_8$-cycloalkyl, preferably $C_5$–$C_7$cycloalkyl and particularly $C_5$–$C_6$cycloalkyl, for example cyclopropyl, cyclobutyl, cyclopentyl, cyclohexyl, cycloheptyl and cyclooctyl. $R^9$ may be $C_4$–$C_{20}$cycloalkylalkyl or -alkylcycloalkyl, preferably $C_6$–$C_{15}$cycloalkylalkyl or -alkylcycloalkyl, the cycloalkyl preferably being cyclopentyl or cyclohexyl. Examples are cyclopentyl- or cyclohexylmethyl, cyclopentyl- or cyclohexylethyl, cyclopentyl- or cyclohexylpropyl, cyclopentyl- or cyclohexylbutyl, methyl-, dimethyl-, ethyl-, n-propyl-, i-propyl-, n-butyl-, i-butyl- or t-butylcyclopentyl or -cyclohexyl. $R^9$ may be $C_5$–$C_{20}$alkylcycloalkylalkyl, preferably $C_7$–$C_{16}$alkylcycloalkylalkyl, for example (methylcyclopentyl)-methyl or -ethyl or (methylcyclohexyl)methyl or -ethyl.

$R^9$ may also be $C_6$–$C_{14}$aryl, preferably $C_6$–$C_{10}$aryl, for example naphthyl and particularly phenyl. $R^9$ may also be $C_7$–$C_{20}$aralkyl or -alkaryl, preferably $C_7$–$C_{16}$aralkyl or -alkaryl. The aryl here is preferably a phenyl radical. Examples are benzyl, phenylethyl, phenylpropyl, phenylbutyl, methylphenyl, ethylphenyl, propylphenyl and butylphenyl. $R^9$ may also be $C_8$–$C_{20}$alkaralkyl, preferably $C_8$–$C_{16}$alkaralkyl, in which the aryl is preferably phenyl. Examples are methylbenzyl, (methylphenyl)ethyl, (methylphenyl)propyl, (methylphenyl)butyl, ethylbenzyl and propylbenzyl.

$R^{10}$ may have one of the meanings given for $R^9$, including the preferences for $R^9$. $R^{10}$ may be $C_1$–$C_{20}$haloalkyl, preferably $C_1$–$C_{12}$haloalkyl and particularly $C_1$–$C_6$haloalkyl, it being possible for the alkyl group to be partially or fully substituted by halogen, preferably Cl and/or F. Examples are chloromethyl, dichloromethyl, trichloromethyl, fluorodichloromethyl, difluorochloromethyl, trifluoromethyl, 2,2-dichloroethyl, 2,2-difluoroethyl, 1,1,1-trichloroethyl, 1,1,1-trifluoroethyl, pentafluoroethyl, chloropropyl, fluoropropyl, perfluoropropyl, chlorobutyl, fluorobutyl, perfluorobutyl, chloropentyl, perfluoropentyl and perfluorohexyl.

$R^9$ and $R^{10}$ may be linear or branched $C_2$–$C_{20}$alkenyl, preferably $C_2$–$C_{12}$alkenyl and particularly $C_2$–$C_6$alkenyl. Examples are vinyl, crotonyl, allyl, but-1-en-1-yl, but-1-en-4-yl, pent-1-en-1-yl, pent-2-en-2-yl, hex-1-en-yl, hex-3-en-3-yl and hex-1-en-6-yl. $R^{10}$ may also be $C_2$–$C_{20}$alkyl, preferably $C_2$–$C_{12}$alkyl and particularly $C_2$–$C_6$alkyl which is interrupted by —CO—, for example acetylmethyl, propionylmethyl, acetylethyl and propionylethyl.

If Y is —SO$_2$—, —CO— or —CS—, $R^{10}$ may also be the NR$^{13}$R$^{14}$ group, in which $R^{13}$ and $R^{14}$, independently of one another, have one of the meanings given for $R^9$, including preferred embodiments. $R^{13}$ and $R^{14}$ are preferably a hydrogen atom or $C_1$–$C_{12}$alkyl, particularly $C_1$–$C_6$alkyl, for example hexyl, pentyl, butyl, propyl and particularly ethyl or methyl.

$R^9$ and $R^{10}$ together may preferably be $C_2$–$C_8$alkylene which is unsubstituted or substituted by halogen, for example 1,2-ethylene, 1,3-propylene, 1,4-butylene, 1-dimethylethylene, 1-methyl-1-chloromethylethylene or 1-diethylethylene.

Y is preferably —CO—, —COO— or —SO$_2$—. $R^4$ in the —Si($R^4$)$_3$ group is particularly methyl.

Unsubstituted $C_1$–$C_{20}$alkanediyl Z may be linear or branched. It preferably has 1-8, in particular 1–4, C atoms. Examples of this are methylene, dimethylene, trimethylene, tetramethylene, pentamethylene, hexamethylene, octamethylene, 1,2-propylene, 1,2-butylene or 2,3-dimethyl-1,4-butylene. Z may be substituted by —COOR$^4$, —CN or halogen. Examples of these are 2-methoxycarbonylethylene, 3-ethoxycarbonyl-1,2-propylene, 2-cyanoethylene, 1-chloroethylene or dichloromethylene.

Preferred titanocenes of the formula I are those in which $R^2$ and $R^3$ are substituted by a radical of the formula II, in which $R^5$, $R^6$, $R^7$ and $R^8$, independently of one another, are hydrogen, $C_1$–$C_{12}$alkyl, $C_2$–$C_5$alkenyl, $C_7$–$C_9$phenylalkyl, $C_7$–$C_{10}$alkylphenyl, phenyl, 2-furyl, $C_5$– or $C_6$cycloalkyl, $C_5$– or $C_6$cycloalkenyl, $C_2$–$C_8$alkanoyl, $C_2$–$C_5$alkoxycarbonyl, —CHO or —Si(R$^4$)$_3$, in which R$^4$ is $C_1$–$C_8$alkyl or phenyl, each of which is unsubstituted or substituted by $C_2$–$C_8$dialkylamino, bis(2-methoxyethyl)amino, morpholino, piperidino, $C_1$–$C_{12}$alkoxy, ‐(OCH$_2$CH$_2$)$_p$– OC$_1$–$C_{12}$alkyl where p=1-3, 1,3-dioxolan-2-yl, —OCH$_2$CH$_2$O—, $C_2$–$C_8$alkanoyloxy, $C_1$–$C_8$alkoxycarbonyl, halogen, cyano, $C_1$–$C_4$alkylthio or —Si(CH$_3$)$_3$, and Z is unsubstituted $C_1$–$C_8$alkanediyl.

A further preferred class of titanocenes of the formula I in which R$^2$ and R$^3$ are substituted by a radical of the formula II is formed by compounds in which R$^5$, R$^6$, R$^7$ and R$^8$, independently of one another, are hydrogen, $C_1$–$C_8$alkyl, $C_2$–$C_4$alkenyl, phenyl, 2-furyl or —Si(R$^4$)$_3$, in which R$^4$ is $C_1$–$C_4$alkyl, each of which is unsubstituted or substituted by $C_2$–$C_8$dialkylamino, morpholino, $C_1$–$C_4$alkoxy, 1,3-dioxolan-2-yl or cyano, and Z is unsubstituted $C_1$–$C_4$alkanediyl, in particular those in which R$^5$, R$^6$, R$^7$ and R$^8$, independently of one another, are hydrogen or $C_1$–$C_4$alkyl, and those in which R$^6$ and R$^7$ are hydrogen.

A further preferred class of titanocenes of the formula I is formed by compounds in which R$^2$ and R$^3$ are substituted by a group of the formula IIa, in which Y is —CO—, —CS—, —COO— or —SO$_2$—, R$^9$ is hydrogen, $C_1$–$C_{12}$alkyl, $C_2$–$C_5$alkenyl, $C_5$–$C_8$cycloalkyl, $C_6$–$C_{18}$cycloalkylalkyl, $C_6$–$C_{18}$alkylcycloalkyl, $C_7$–$C_{18}$alkylcycloalkylalkyl, $C_7$–$C_{16}$aralkyl or $C_8$–$C_{16}$alkaralkyl, each of which is unsubstituted or substituted by $C_1$–$C_{12}$alkoxy or tetrahydrofuryl, R$^{10}$ has one of the meanings given for R$^9$ or is $C_6$–$C_{10}$aryl, $C_6$–$C_{10}$haloaryl, $C_7$–$C_{18}$alkaryl or $C_1$–$C_{12}$haloalkyl, or in the case where Y is —CO— or —SO$_2$— R$^{10}$ is alternatively —NR$^{13}$R$^{14}$, in which R$^{13}$ and R$^{14}$, independently of one another, are hydrogen, $C_1$–$C_{12}$alkyl, phenyl, benzyl or cyclohexyl, or R$^{13}$ and R$^{14}$ together are $C_4$–$C_5$alkylene or 3-oxapentamethylene, or R$^9$ and R$^{10}$ together are $C_2$–$C_8$alkylene, and Z is unsubstituted $C_1$–$C_8$alkanediyl.

Of these, those compounds are preferred in which R$^9$ is hydrogen, $C_1$–$C_{12}$alkyl, cyclohexyl, cyclohexylmethyl, 2-tetrahydrofurylmethyl, $C_2$–$C_8$alkoxyalkyl, allyl or $C_7$–$C_9$aralkyl, R$^{10}$ is $C_1$–$C_{18}$alkyl, $C_1$–$C_4$haloalkyl, cyclohexyl, $C_6$–$C_{10}$aryl, halophenyl or $C_7$–$C_{18}$alkaryl, or $R^9$ and $R^{10}$ together are $C_2$–$C_6$alkylene, Y is —CO—, —COO— or —SO$_2$— or the radical —Y—$R^{10}$ is a —CO—NHR$^{13}$, —CS—NHR$^{13}$, —CO—NR$^{13}$R$^{14}$ or —SO$_2$—NR$^{13}$R$^{14}$ group, in which $R^{13}$ is $C_1$–$C_{12}$alkyl or phenyl, $R^{14}$ is $C_1$–$C_{12}$alkyl or $R^{13}$ and $R^{14}$ together are $C_4$–$C_5$alkylene or 3-oxapentamethylene, and Z is unsubstituted $C_1$–$C_8$alkanediyl, in particular those compounds in which $R^9$ is hydrogen, $C_1$–$C_8$alkyl or $C_7$–$C_9$aralkyl, $R^{10}$ is $C_1$–$C_{18}$alkyl, trifluoromethyl, phenyl, or phenyl which is substituted by halogen or $C_1$–$C_{12}$alkyl, or $R^9$ and $R^{10}$ together are $C_2$–$C_6$alkylene, Y is —CO— or —SO$_2$—, and Z is unsubstituted $C_1$–$C_4$alkanediyl.

Of the compounds of the formula I in which $R^2$ and $R^3$ are substituted by a group of the formula IIb, those are preferred in which $R^{10}$ and $R^{11}$ together are $C_2$–$C_8$alkanediyl, $C_2$–$C_8$alkenediyl, $C_6$–$C_{14}$arenediyl, cyclohexanediyl or $C_7$–$C_{12}$bicycloalkanediyl, Y is —CO—, and Z is unsubstituted $C_1$–$C_4$alkanediyl.

Examples of individual compounds of the formula I are:

bis(cyclopentadienyl)-bis[2,6-difluoro-3-(2-(1H-pyrr-1-yl)ethyl)phenyl]titanium
bis(cyslopentadienyl)-bis[2,6-difluoro-3-(3-(1H-pyrr-1-yl)propyl)phenyl]titanium
bis(cyclopentadienyl)-bis[2,6-difluoro-3-((1H-pyrr-1-yl)methyl)phenyl]titanium
bis(methylcyclopentadienyl)-bis[2,6-difluoro-3-((1H-pyrr-1-yl)methyl)phenyl]-titanium
bis(cyclopentadienyl)-bis[2,6-difluoro-3-((2,5-dimethyl-1H-pyrr-1-yl)methyl)-phenyl]-titanium
bis(cyclopentadienyl)-bis[2,6-difluoro-3-((2-isopropyl-5-methyl-1H-pyrr-1-yl)methyl)-phenyl]titanium
bis(cyclopentadienyl)-bis[2,6-difluoro-3-((2-(2-methoxyethyl)-5-methyl-1H-pyrr-1-yl)-methyl)-phenyl]titanium
bis(cyclopentadienyl)-bis[2,6-difluoro-3-((3-trimethylsilyl-2,5-dimethyl-1H-pyrr-1-yl)-methyl)phenyl]titanium
bis(cyclopentadienyl)-bis[2,6-difluoro-3-((2,5-dimethyl-3-(bis(2-methoxyethyl)-aminomethyl)-1H-pyrr-1-yl)methyl)phenyl]titanium
bis(cyclopentadienyl)-bis[2,6-difluoro-3-((2,5-bis(morpholinomethyl)-1H-pyrr-1H-pyrr-1-yl)-methyl)-phenyl]titanium
bis(cyclopentadienyl)-bis[2,6-difluoro-3-((2,5-dimethyl-3-(1,3-dioxolan-2-yl)-1H-pyrr-1-yl)methyl)phenyl]titanium
bis(cyclopentadienyl)-bis[2,6-difluoro-4-((2,5-dimethyl-1H-pyrr-1-yl)methyl)phenyl]-titanium
bis(cyclopentadienyl)-bis[2,6-difluoro-3-methyl-4-(2-(1H-pyrr-1-yl)ethyl)phenyl]titanium
bis(cyclopentadienyl)-bis[2,6-difluoro-3-((2,3,4,5-tetramethyl-1H-pyrr-1-yl)methyl)-phenyl]titanium
bis(cyclopentadienyl)-bis[2,3,5,6-tetrafluoro-4-(3-(1H-pyrr-1-yl)propyl)phenyl]titanium
bis(cyclopentadienyl)-bis[2,6-difluoro-3-(2-(1H-pyrr-1-yl)propyl)phenyl]titanium
bis(cyclopentadienyl)-bis[2,6-difluoro-3-(1-methyl-2-(1H-pyrr-1-yl)ethyl)phenyl]titanium
bis(cyclopentadienyl)-bis[2,6-difluoro-3-(3-(2H-isoindol-2-yl)propyl)phenyl]titanium
bis(cyclopentadienyl)-bis[2,6-difluoro-3-(2-(4,5,6,7-tetrahydro-2H-isoindol-2-yl)ethyl)-phenyl]titanium
bis(cyclopentadienyl)-bis[2,6-difluoro-3-(6-(9H-carbazol-9-yl)hexyl)phenyl]titanium
bis(cyclopentadienyl)-bis[2,6-difluoro-3-(3-(2,3,4,5,6,7,8,9-octahydro-1H-carbazol-9-yl)-propyl)-phenyl]titanium
bis(cyclopentadienyl)-bis[2,6-difluoro-3-(3-(4,5,6,7-tetrahydro-2-methyl-1H-indol-1-yl)-propyl)phenyl]-titanium
bis(cyclopentadienyl)-bis[2,6-difluoro-3-(2-(5-methoxy-2-methyl-1H-indol-1-yl)ethyl-phenyl]titanium
bis(cyclopentadienyl)-bis[2,6-difluoro-3-(3-(2-methyl-1H-indol-1-yl)propyl)phenyl]-titanium
bis(cyclopentadienyl)-bis[2,6-difluoro-3-(4-(1,4,5,6-tetrahydro-2-methylcyclopenta[b]-pyrr-1-yl)butyl)-phenyl]titanium
bis(cyclopentadienyl)-bis[2,6-difluoro-3-(4-(2,3,4,5,6,7-hexahydro-1H-di-cyclopenta[b,d]-pyrr-1-yl)-2,3-dimethyl)butyl)phenyl]titanium
bis(cyclopentadienyl)-bis[2,6-difluoro-3-((acetylamino)-methyl)phenyl]titanium
bis(cyclopentadienyl)-bis[2,6-difluoro-3-(2-propionylamino)ethyl)phenyl]titanium
bis(cyclopentadienyl)-bis[2,6-difluoro-3-(3-(acetylamino)propyl)phenyl]titanium
bis(cyclopentadienyl)-bis[2,6-difluoro-3-(4-(pivaloylamino)butyl)phenyl]titanium
bis(cyclopentadienyl)-bis[2,6-difluoro-3-(2-(2,2-dimethylpentanoylamino)ethyl)phenyl]-titanium
bis(cyclopentadienyl)-bis[2,6-difluoro-3-(3-(benzoylamino)propyl)phenyl]titanium
bis(cyclopentadienyl)-bis[2,6-difluoro-3-(((2,2-dimethylpentanoylamino)methyl)phenyl]-titanium
bis(cyclopentadienyl)-bis[2,6-difluoro-3-(2-(2,2-dimethyl-3-chloropropanoylamino)ethyl)-phenyl]titanium
bis(cyclopentadienyl)-bis[2,6-difluoro-3-((2,2-dimethyl-3-ethoxypropanoylamino)-methyl)phenyl]titanium
bis(cyclopentadienyl)-bis[2,6-difluoro-3-(2-(lauroylamino)ethyl)phenyl]titanium
bis(cyclopentadienyl)-bis[2,6-difluoro-3-((N-hexyl-(2,2-dimethylpentanoyl)amino)-methyl)phenyl]titanium
bis(cyclopentadienyl)-bis[2,6-difluoro-3-((N-ethyl-propionylamino)methyl)phenyl]-titanium
bis(cyclopentadienyl)-bis[2,6-difluoro-3-(2-(N-methylacetylamino)ethyl)phenyl]titanium
bis(cyclopentadienyl)-bis[2,6-difluoro-3-(3-(N-(2-methoxyethyl)isobutyrylamino)propyl)-phenyl]-titanium
bis(cyclopentadienyl)-bis[2,6-difluoro-3-(2-(N-cyclohexyl-(3-phenylpropanoyl)amino-ethyl)-phenyl]titanium
bis(cyclopentadienyl)-bis[2,6-difluoro-3-(2-(N-(oxolan-2-ylmethyl)-(4-toluyl)amino)-ethyl)phenyl]titanium
bis(cyclopentadienyl)-bis[2,6-difluoro-3-(3-(N-allylacetylamino)propyl)phenyl]titanium
bis(cyclopentadienyl)-bis[2,6-difluoro-3-(2-(N-benzyldecanoylamino)propyl)phenyl]-titanium
bis(cyclopentadienyl)-bis[2,6-difluoro-3-((N-butyl-(4-tolylsulfonyl)amino)methyl)-phenyl]titanium
bis(cyclopentadienyl)-bis[2,6-difluoro-3-(2-(N-allylmethylsulfonylamino)ethyl)-phenyl]titanium
bis(cyclopentadienyl)-bis[2,6-difluoro-3-(3-(N-isobutylphenylsulfonylamino)propyl)-phenyl]titanium
bis(cyclopentadienyl)-bis[2,6-difluoro-3-((methylsulfonylamino)methyl)phenyl]titanium
bis(cyclopentadienyl)-bis[2,6-difluoro-3-(3-(ethylsulfonylamino)propyl)phenyl]titanium
bis(cyclopentadienyl)-bis[2,6-difluoro-3-(2-butylsulfonylamino)ethyl)phenyl]titanium
bis(cyclopentadienyl)-bis[2,6-difluoro-3-(3-(4-tolylsulfonylamino)propyl)phenyl]titanium bis(cyclopentadienyl)-bis[2,6-difluoro-3-(3-(methylsulfonylamino)-2-methylpropyl)-phenyl]titanium
bis(cyclopentadienyl)-bis[2,6-difluoro-3-((hexadecylsulfonylamino)methyl)phenyl]-titanium
bis(cyclopentadienyl)-bis[2,6-difluoro-3-(3-(2-naphthylsulfonylamino)propyl)-phenyl]titanium
bis(cyclopentadienyl)-bis[2,6-difluoro-3-(2-(3,3-diallyl-2-pyrrolidon-1-yl)ethyl)-phenyl]titanium
bis(cyclopentadienyl)-bis[2,6-difluoro-3-((3,3-dimethyl-2-azetidonon-1-yl)methyl)-phenyl]titanium
bis(cyclopentadienyl)-bis[2,6-difluoro-3-(3-(N-(2,3-dihydro-1,2-benzisothiazol-3-one-1,1-dioxid-2-yl))propyl)phenyl]titanium
bis(cyclopentadienyl)-bis[2,6-difluoro-4-(2-(N-phthalimido)ethyl)phenyl]titanium
bis(cyclopentadienyl)-bis[2,6-difluoro-3-(2-(phthalimido)ethyl)phenyl]titanium
bis(cyclopentadienyl)-bis[2,6-difluoro-3-(3-(pyrrolidine-2,5-dion-1-yl)propyl)phenyl]-titanium
bis(cyclopentadienyl)-bis[2,6-difluoro-3-(2-(3,4-dimethyl-3-pyrroline-2,5-dion-1-yl)-propyl)phenyl]titanium
bis(cyclopentadienyl)-bis[2,6-difluoro-3-(2-(3,3-dimethyl-2-pyrrolidinon-1-yl)ethyl)-phenyl]titanium
bis(cyclopentadienyl)-bis[2,6-difluoro-3-(2-(3,3-diallyl-2-piperidinon-1-yl)ethyl)-phenyl]titanium
bis(cyclopentadienyl)-bis[2,6-difluoro-3-(3-(6,6-diphenyl-2-piperidinon-1-yl)propyl)-phenyl]titanium
bis(pentamethylcyclopentadienyl)-bis[2,6-difluoro-3-(4-(3-allyloxymethyl-3-methyl-2-azetidinon-1-yl)butyl)phenyl]titanium
bis(cyclopentadienyl)-bis[2,6-difluoro-3-[6-(3-ethoxymethyl-3-methyl-2-azetidinon-1-yl)-hexyl]phenyl]titanium
bis(methylcyclopentadienyl)-bis[2,6-difluoro-4-(3-(3,3-diallyl-2-pyrrolidinon-1-yl)-propyl)methylphenyl]titanium
bis(cyclopentadienyl)-bis[2,6-difluoro-3-(2-(isobutoxycarbonylamino)ethyl)phenyl]-titanium
bis(cyclopentadienyl)-bis[2,6-difluoro-3-((ethoxycarbonylamino)methyl)phenyl]titaniium
bis(cyclopentadienyl)-bis[2,6-difluoro-3-(3-((2-chloroethoxy)carbonylamino)propyl)-phenyl]-titanium
bis(cyclopentadienyl)-bis[2,6-difluoro-3-(4-(phenoxycarbonylamino)butyl)phenyl]-titanium
bis(cyclopentadienyl)-bis[2,6-difluoro-3-(2-(phenylthiocarbonylamino)ethyl)phenyl]-titanium
bis(cyclopentadienyl)-bis[2,6-difluoro-3-(2-(3-phenylthioureido)ethyl)phenyl]titanium
bis(cyclopentadienyl)-bis[2,6-difluoro-3-(3-(3-butylthioureido)propyl)phenyl]titanium
bis(cyclopentadienyl)-bis[2,6-difluoro-3-((3-phenylureido)methyl)phenyl]titanium
bis(cyclopentadienyl)-bis[2,6-difluoro-3-(2-(3-butylureido)ethyl)phenyl]titanium
bis(cyclopentadienyl)-bis[2,6-difluoro-3-(2-(3,3-dimethylureido)ethyl)phenyl]titanium
bis(cyclopentadienyl)-bis[2,6-difluoro-3-(2-(N,N-diacetylamino)ethyl)phenyl]titanium
bis(cyclopentadienyl)-bis[2,6-difluoro-3-((N-phenylsulfonyl-N-acetylamino)methyl)-phenyl]titanium
bis(cyclopentadienyl)-bis[2,6-difluoro-3-(((trifluoromethylsulfonyl)amino)methyl)-phenyl]titanium
bis(cyclopentadienyl)-bis[2,6-difluoro-3-(2-(trifluoroacetylamino)ethyl)phenyl]titanium
bis(cyclopentadienyl)-bis[2,6-difluoro-3-((N-methyl-(4-dodecylphenyl)sulfonylamino)-methyl)phenyl]titanium
bis(cyclopentadienyl)-bis[2,6-difluoro-3-(4-(N-ethyl(4-bromophenyl)sulfonylamino)-butyl)phenyl]titanium
bis(methylcyclopentadienyl)-bis[2,6-difluoro-3-(2-hexadecylsulfonylamino)ethyl)phenyl]-titanium
bis(trimethylsilylcyclopentadienyl)-bis[2,6-difluoro-3-2-(N-(2-ethylhexyl)-(4-tolylsulfonylamino)ethyl)-phenyl]titanium
bis(cyclopentadienyl)-bis[2,6-difluoro-3-((N-(2-methoxyethyl)-(trimethylsilyl)amino)-methyl)phenyl]-titanium
bis(cyclopentadienyl)-bis[2,6-difluoro-3-((3-(N-butyl)-(1,1,2-trimethylpropyl)dimethylsilylamino)propyl)-phenyl]titanium
bis(cyclopentadienyl)-bis[2,6-difluoro-3-((2,2,5,5-tetramethyl-1,2,5-azadisilolidin-1-yl)-methyl)phenyl]-titanium
bis(cyclopentadienyl)-bis[2,6-difluoro-3-(2-(cyclohexylcarbonylamino)ethyl)phenyl]-titanium
bis(cyclopentadienyl)-bis[2,3,5,6-tetrafluoro-4-((butyrylamino)methyl)phenyl]titanium
bis(cyclopentadienyl)-bis[2,6-difluoro-3-(2-(3,4-xyloylamino)ethyl)phenyl]titanium
bis(cyclopentadienyl)-bis[2,6-difluoro-3-(2-(2-chloromethyl-2-methyl-3-chloropropanoylamino)-propyl)phenyl]titanium
bis(cyclopentadienyl)-bis[2,6-difluoro-3-((2,2-dimethyl-3-allyloxypropanoylamino)-methyl)-phenyl]titanium
bis(cyclopentadienyl)-bis[2,6-difluoro-3-(2-(2,2-dimethyl-3-ethoxypropanoylamino)-ethyl)phenyl]titanium
bis(cyclopentadienyl)-bis[2,6-difluoro-3-(2-(2,2-dimethyl-3-chloropropanoylamino)-butyl)phenyl]titanium
bis(cyclopentadienyl)-bis[2,6-difluoro-3-(2-(N-cyclohexylmethyl-pivaloylamino)ethyl)-phenyl]-titanium
bis(cyclopentadienyl)-bis[2,6-difluoro-3-((N-(oxolan-2-ylmethyl)-(2,2-dimethylpentanoyl)amino)methyl)-phenyl]titanium
bis(cyclopentadienyl)-bis[2,6-difluoro-3-(2-(N-(1,3-dimethylbutyl)-(2,2-dimethylbutanoyl)amino)ethyl)-phenyl]titanium
bis(cyclopentadienyl)-bis[2,6-difluoro-3-(3-(N-cyclohexyl-(2,2-dimethylpropanoyl)-amino)propyl)-phenyl]titanium
bis(cyclopentadienyl)-bis[2,6-difluoro-3-(3-(N-isopropyl-(2,2-dimethylpropanoyl)amino)-decyl)phenyl]-titanium
bis(cyclopentadienyl)-bis[2,6-difluoro-3-(2-(N-isopropyl-(4-toluyl)amino)ethyl)phenyl]-titanium
bis(cyclopentadienyl)-bis[2,6-difluoro-3-(2-carbethoxy-3-(N-allylacetylamino)propyl)-phenyl]titanium
bis(cyclopentadienyl)-bis[2,6-difluoro-3-((N-(3-oxaheptyl)-(2,2-dimethylpentanoyl)-amino)-methyl)phenyl]-titanium
bis(cyclopentadienyl)-bis[2,6-difluoro-3-((N-ethyl-(5-carbethoxypentanoyl)amino)-methyl)phenyl]-titanium
bis(cyclopentadienyl)-bis[2,6-difluoro-3-(2-((4-carboxybutanoyl)amino)ethyl)phenyl]-titanium
bis(cyclopentadienyl)-bis[2,6-difluoro-4-methyl-3-(N-(3,7-dimethyl-7-methoxyoctyl)-benzoylamino)-propyl)phenyl]titanium
bis(cyclopentadienyl)-bis[2,6-difluoro-3-(3-(3,4-tetramethylene-2-pyrrolidinon-1-yl)-propyl)phenyl]-titanium
bis(cyclopentadienyl)-bis[2,6-difluoro-3-(3-(benzo[c]-2-pyrrolidinon-1yl)propyl)phenyl]-titanium The titanocenes of the formula I can be prepared by known processes or analogously to known processes by reacting 1 mole of a compound of the formula IV

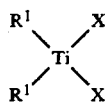

in which R¹ is as defined above and X is halogen, particularly chlorine, with one mole of LiR² and with one mole of LiR³ or with 2 moles of LiR², R² and R³ being as defined above, and then isolating the compounds of the formula I in a manner known per se.

The known processes are described, for example, in J. Organometal. Chem., 2 (1964) 206-212, J. Organometal. Chem., 4 (1965) 445-446, and in EP-A-122,223.

The starting compounds of the formula IV, in which X is particularly chlorine, are known or can be obtained by analogous processes by reacting $TiCl_4$ with the sodium compounds $NaR^1$. Lithium compounds $LiR^2$ and $LiR^3$ are novel. They can be prepared, for example, by processes known per se by reacting butyllithium with $HR^2$ or $HR^3$. This is described in greater detail in the examples below.

The compounds $HR^2$ and $HR^3$ can be prepared analogously to the processes known per se.

Preferably, the appropriate aminoalkylfluoroarenes are first prepared, for example by reducing the corresponding nitriles. The primary amines can be converted into pyrrole derivatives which contain a radical of the formula II using 1,4-dicarbonyl compounds or using 2,5-dimethoxytetrahydrofuran.

The radical $R^9$ can be introduced by reductive amination of the corresponding aldehydes or ketones. The radicals $R^{10}Y-$ and $R^{11}Y-$ can be introduced by means of the halogen compounds $R^{10}-Y-X$ and $R^{11}-Y-X$ or by means of the acid anhydrides $(R^{10}Y)_2O$.

The scheme for the preparation of 1-(2,4-difluorophenylmethyl)pyrrole is shown here as an example of the preparation of a compound $HR^2$:

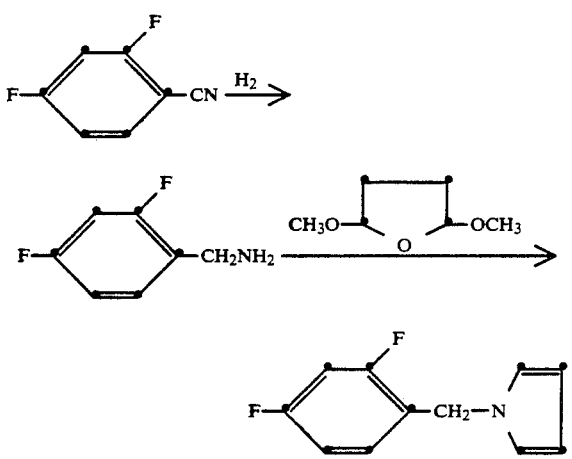

The preparation of the metallocenes of the formula I from the compounds $HR^2$ and $HR^3$ is generally carried out in the presence of inert solvents, for example hydrocarbons or ethers, and under a protective-gas atmosphere. In an embodiment of the process, $LiR^2$ or $LiR^3$ is first prepared by reacting $HR^2$ or $HR^3$ respectively with butyllithium in an ether as solvent, for example tetrahydrofuran, at temperatures around −78° C. The appropriate titanocene dihalide is then added to the cooled reaction mixture, the cooling is removed, and the mixture is allowed to warm to room temperature. The reaction mixture is then filtered, if necessary after addition of solvents, and the titanocene according to the invention is isolated from the solution by precipitation or evaporation of the solvent.

In another embodiment, a mixture of $HR^2$ and titanocene chloride in tetrahydrofuran is reacted at −25° to −10° C. with a solution of a lithium amide, for example with lithium diisopropylamide. The titanocene is isolated in the customary manner after removal of the LiCl formed.

The titanocenes are generally crystalline, usually orange compounds which are distinguished by high thermal stability and only decompose at high temperatures. No decomposition is observed either under the action of air or under the action of water. The compounds can be dissolved, even in relatively high amounts, in curable compositions, and therefore offer valuable applicational properties. The compounds are also readily soluble in solvents, and can be incorporated in the form of solutions into curable compositions, after which the solvent is removed if necessary.

The compounds are stable on storage in the dark and can be handled without a protective gas. They are highly suitable alone as highly effective photoinitiators for the photoinduced polymerization of ethylenically unsaturated compounds. In this case, they are distinguished by very high photosensitivity and effectiveness over a wide wavelength range of from about 200 nm (UV light) to about 600 nm. Furthermore, the titanocenes are also capable of effectively initiating the polymerization under the influence of heat, warming to between 170° C. and 240° C. being expedient. It is of course also possible to use the action of light and warming for the polymerization, warming after irradiation allowing lower temperatures, for example 80°-150° C., for the polymerization.

The invention furthermore relates to a radiation-polymerizable composition containing (a) at least one non-volatile, monomeric, oligomeric or polymeric compound containing at least one polymerizable ethylenically unsaturated double bond, and (b) at least one titanocene of the formula I as photoinitiator.

The compositions may contain further photoinitiators (c) which are different from (b), for example those of the benzophenone, benzoin alkyl ether, benzil ketal, 4-aroyl-1,3-dioxolane, dialkoxyacetophenone, α-hydroxy- or α-aminoacetophenone, α-hydroxycycloalkyl phenyl ketone type, or mixtures thereof. The advantage is that lower amounts of the titanocenes according to the invention can be used and nevertheless equal or improved photosensitivities can be achieved.

The added amount of titanocenes according to the invention depends essentially on economic points of view, their solubilities and on the desired sensitivity. In general, 0.01 to 20, preferably 0.05–10 and particularly 0.1 to 5,% by weight are used, relative to component (a).

Compounds which are suitable as component (a) are ethylenically unsaturated monomeric, oligomeric and polymeric compounds which react by photopolymerization to form high-molecular-weight products, during which they modify their solubility.

Esters of ethylenically unsaturated carboxylic acids and polyols or polyepoxides, and polymers containing ethylenically unsaturated groups in the chain or in side groups, for example unsaturated polyesters, polyamides and polyurethanes, and copolymers thereof, polybutadiene and butadiene copolymers, polyisoprene and isoprene copolymers, polymers and copolymers containing (meth)acrylic groups in the side chains, and mixtures of two or more such polymers, for example, are particularly suitable.

Examples of unsaturated carboxylic acids are acrylic acid, methacrylic acid, crotonic acid, itaconic acid, cinnamic acid, unsaturated fatty acids, such as linolenic acid or oleic acid. Acrylic acid and methyacrylic acid are preferred.

Suitable polyols are aromatic and particularly aliphatic and cycloaliphatic polyols. Examples of aromatic polyols are hydroquinone, 4,4′-dihydroxydiphenyl, 2,2-di(4-hydroxyphenyl)propane, and novolaks and resols. Examples of polyepoxides are those based on the polyols mentioned, particularly on the aromatic polyols and epichlorohydrin. Furthermore, polymers or copolymers which contain hydroxyl groups in the polymer chain or side groups, for example polyvinyl alcohol and copolymers thereof, or hydroxyalkyl polymethacrylates or copolymers thereof, are also suitable as polyols. Further suitable polyols are oligoesters containing hydroxyl end groups.

Examples of aliphatic and cycloaliphatic polyols are alkylene diols preferably having 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of, preferably, 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be partially or fully esterified with one or different unsaturated carboxylic acids, it being possible, in partial esters, for the free hydroxyl groups to be modified, for example etherified or esterified with other carboxylic acids.

Examples of esters are: trimethylolpropane triarcrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol having molecular weights of 200–1500, or mixtures thereof.

Compounds which are suitable as component (a) are also the amides of identical or different unsaturated carboxylic acids of aromatic, cycloaliphatic and aliphatic polyamines preferably having 2 to 6, particularly 2 to 4, amino groups. Examples of such polyamines are ethylenediamine, 1,2- or 1,3-propylenediamine, 1,2-, 1,3,- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetramine, di($\beta$-aminoethoxy)- or di($\beta$-aminopropoxy)ethane. Further suitable polyamines are polymers and copolymers containing amino groups in the side chain and oligoamides containing amino end groups.

Examples of unsaturated amides of this type are: methylene bisacrylamide, 1,6-hexamethylene bisacrylamide, diethylenetriamine trismethacrylamide, bis(methacrylamidopropoxy)ethane, $\beta$-methacrylamidoethyl methacrylate and N-[($\beta$-hydroxyethoxy)ethyl]acrylamide.

Suitable unsaturated polyesters and polyamides are derived, for example, from maleic acid and diols or diamines. Maleic acid may be partially replaced by other dicarboxylic acids. They can be employed together with ethylenically unsaturated comonomers, for example styrene. Polyesters and polyamides may also be derived from dicarboxylic acids and ethylenically unsaturated diols or diamines, particularly from those having relatively long chains with, for example, 6 to 20 C atoms. Examples of polyurethanes are those built up from saturated or unsaturated diisocyanates and unsaturated or saturated diols.

Polybutadiene and polyisoprene and copolymers thereof are known. Examples of suitable comonomers are olefins, such as ethylene, propene, butene, hexene, (meth)acrylates, acrylonitrile, styrene or vinyl chloride. Polymers containing (meth)acrylate groups in the side chain are likewise known. They may be, for example, products of the reaction of epoxy resins based on novolak with (meth)acrylic acid, homopolymers or copolymers of polyvinyl alcohol or hydroxyalkyl derivatives thereof which have been esterified with (meth)acrylic acid, or homopolymers and copolymers of (meth)acrylates which have been esterified with hydroxyalkyl (meth)acrylates.

The photopolymerizable compounds may be employed alone or in any desired mixtures. Mixtures of polyol (meth)acrylates are preferably used.

Binders may also be added to the compositions according to the invention, which is particularly expedient if the photopolymerizable compounds are liquid or viscous substances. The amount of binder can be, for example, 5–95, preferably 10–90 and particularly 50–90, % by weight, relative to the total composition. The choice of binder depends on the area of application and properties required for this purpose, such as ability to be developed in aqueous and organic solvent systems, adhesion to substrates and oxygen sensitivity.

Examples of suitable binders are polymers having a molecular weight of from about 5000–2,000,000, preferably 10,000 to 1,000,000. Examples are: homopolymeric and copolymeric acrylates and methacrylates, for example copolymers made from methyl methacrylate/ethyl acrylate/methacrylic acid, poly(alkyl methacrylates), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyethers, such as polyethylene oxide, polypropylene oxide, polytetrahydrofuran; polystyrene, polycarbonate, polyurethane, chlorinated polyolefins, polyvinyl chloride, copolymers made from vinyl chloride/vinylidene chloride, copolymers of vinylidene chloride with acrylonitrile, methyl methacrylate and vinyl acetate, polyvinyl acetate, copoly(ethylene/vinyl acetate), polyamides, such as polycaprolactam and poly(hexamethyleneadipamide), polyesters, such as poly(ethylene glycol terephthalate) and poly(hexamethylene glycol succinate).

The compositions according to the invention are suitable as coating agents for substrates of all types, for example wood, paper, ceramics, plastics, such as polyester and cellulose acetate films, and metals, such as copper and aluminium, in which a protective layer or photographic image is to be applied by photopolymerization. The present invention furthermore relates to the coated substrates and to a process for applying photographic images to the substrates. The coated substrates may also be used as recording material for holograms (volume/phase diagram), in which case it is advantageous that wet development is not necessary for this purpose.

The substrates can be coated by applying a liquid composition, a solution or suspension to the substrate. Liquid compositions without solvents are preferred. It may be expedient here to employ the titanocenes according to the invention in the form of a liquid photoinitiator mixture containing other photoinitiators, for example a benzil ketal, a 4-aroyl-1,3-dioxolane, a dialkoxyacetophenone, an α-hydroxy-or α-aminoacetophenone, an α-hydroxycycloalkyl phenyl ketone or mixtures thereof. Liquid mixtures comprising liquid to solid photoinitiators and liquid titanocenes or liquid photoinitiators and syrupy to solid titanocenes are particularly advantageous. These mixtures offer applicational advantages and are distinguished by high stability on storage in the dark.

Examples of benzil ketals are those of the formula

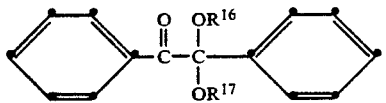

$R^{16}=R^{17}=$ —CH₃

—CH₂CH₃

—(CH₂)₂CH₃

—(CH₂)₃CH₃

—CH₂CH₂CH(CH₃)₂

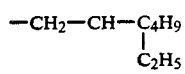

—(CH₂)₉CH₃

—C₁₀H₂₁-iso

—C₁₂H₂₅-n

—C₉H₁₉ to —C₁₁H₂₃ mixture

—C₁₂—H₂₅— to —C₁₅H₃₁ mixture

-continued
—CH₂CH=CH₂

—CH(CH₃)CH=CH₂

—CH₂CH₂OC₃H₇-iso

—CH₂CH₂OC₄H₉

—CH₂CH₂OCH₂CH=CH₂

—CH(CH₃)—CH₂OC₄H₉

—CH₂COOCH₃

—CH₂COOC₄H₉

—CH(CH₃)COOCH₃

—CH₂CH₂COOC₂H₅

—CH(CH₃)CH₂COOCH₃

—CH₂CH₂CH(CH₃)OCH₃

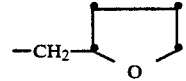

—(CH₂CH₂O)₂CH₃

—(CH₂CH₂O)₂C₂H₅

—(CH₂CH₂O)₂C₄H₉

—(CH₂CH₂O)₃CH₃

—(CH₂CH₂O)₃C₂H₅

—(CH₂CH₂O)₃C₁₂H₂₅

—(CH₂CH₂O)₅C₁₀H₂₁

—(CH₂CH₂O)₈C₉H₁₉ to —C₁₁H₂₃ (mixture)

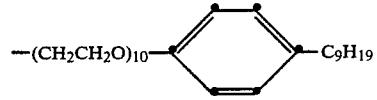

—CH₂CH₂N(C₂H₅)₂

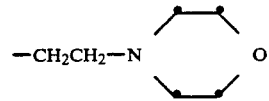

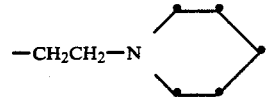

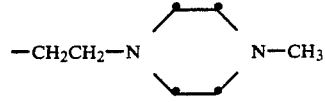

$R^{17}$ = CH₃, $R^{16}$ = C₆H₁₃

$R^{17}$ = CH₃, $R^{16}$ = C₁₀H₂₁

$R^{17}$ = CH₃, $R^{16}$ = —(CH₂CH₂O)₃—C₁₂H₂₅ to —C₁₅H₃₁ (mixture)

$R^{17}$ = CH₃, $R^{16}$ = —(CH₂CH₂O)₅—C₉H₁₉ to —C₁₁H₂₃ (mixture)

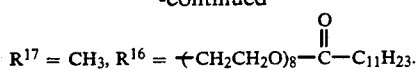

Examples of 4-aroyl-1,3-dioxolanes are:
4-benzoyl-2,2,4-trimethyl-1,3-dioxolane
4-benzoyl-4-methyl-2,2-tetramethylene-1,3-dioxolane
4-benzoyl-4-methyl-2,2-pentamethylene-1,3-dioxolane
cis-trans-4-benzoyl-2,4-dimethyl-2-methoxymethyl-1,3-dioxolane
cis-trans-4-benzoyl-4-methyl-2-phenyl-1,3-dioxolane
4-(4-methoxybenzoyl)-2,2,4-trimethyl-1,3-dioxolane
4-(4-methoxybenzoyl)-4-methyl-2,2-pentamethylene-1,3-dioxolane
4-(4-methylbenzoyl)-2,2,4-trimethyl-1,3-dioxolane
cis-trans-4-benzoyl-2-methyl-4-phenyl-1,3-dioxolane
4-benzoyl-2,2,4,5,5-pentamethyl-1,3-dioxolane
cis-trans-4-benzoyl-2,2,4,5-tetramethyl-1,3-dioxolane,
cis-trans-4-benzoyl-4-methyl-2-pentyl-1,3-dioxolane
cis-trans-4-benzoyl-2-benzyl-2,4-dimethyl-1,3-dioxolane
cis-trans-4-benzoyl-2-(2-furyl)-4-methyl-1,3-dioxolane
cis-trans-4-benzoyl-5-phenyl-2,2,4-trimethyl-1,3-dioxolane
4-(4-methoxybenzoyl)-2,2,4,5,5-pentamethyl-1,3-dioxolane.

Examples of dialkoxyacetophenones are:
$\alpha,\alpha$-dimethoxyacetophenone
$\alpha,\alpha$-diethoxyacetophenone
$\alpha,\alpha$-di-isopropoxyacetophenone
$\alpha,\alpha$-di-(2-methoxyethoxy)acetophenone
$\alpha$-butoxy-$\alpha$-ethoxyacetophenone
$\alpha,\alpha$-dibutoxy-4-chloroacetophenone
$\alpha,\alpha$-diethoxy-4-fluoroacetophenone
$\alpha,\alpha$-dimethoxy-4-methylacetophenone
$\alpha,\alpha$-diethoxy-4-methylacetophenone
$\alpha,\alpha$-dimethoxypropiophenone
$\alpha,\alpha$-diethoxypropiophenone
$\alpha,\alpha$-diethoxybutyrophenone
$\alpha,\alpha$-dimethoxyisovalerophenone
$\alpha,\alpha$-diethoxy-$\alpha$-cyclohexylacetophenone
$\alpha,\alpha$-dipropoxy-4-chloropropiophenone.

Examples of $\alpha$-hydroxy- and $\alpha$-aminoacetophenones are:
2-hydroxy-2-methyl-1-phenyl-1-propanone
2-hydroxy-2-ethyl-1-phenyl-1-hexanone
1-(4-dodecylphenyl)-2-hydroxy-2-methyl-1-propanone
1-(2,4-dimethylphenyl)-2-hydroxy-2-methyl-1-propanone
2-hydroxy-1-(4-methoxyphenyl)-2-methyl-1-propanone
2-hydroxy-2-methyl-1-phenyl-1-butanone
2-dimethylamino-2-methyl-1-phenyl-1-propanone
2-dibutylamino-2-methyl-1-phenyl-1-propanone
1-(4-fluorophenyl)-2-methyl-2-morpholino-1-pentanone
2-methyl-1-(4-methylthiophenyl)-2-morpholino-1-propanone
2-dimethylamino-1-(4-methoxyphenyl)-2-methyl-1-propanone
2-diethylamino-1-(4-diethylaminophenyl)-2-methyl-1-propanone
2-benzyl-2-dimethylamino-1-(4-methoxyphenyl)-1-butanone
2-benzyl-2-dimethylamino-1-(4-tolyl)-1-butanone
2-benzyl-2-dimethylamino-1-phenyl-1-butanone
2-benzyl-2-dimethylamino-1-(4-chlorophenyl)-1-butanone
2-benzyl-2-dimethylamino-1-(3,4-dimethoxyphenyl)-1-butanone
2-benzyl-2-dimethylamino-1-(3,4-dimethoxyphenyl)-1-pentanone
2-benzyl-2-dimethylamino-1-[4-(2-hydroxyethylthio)-phenyl]-1-butanone
2-dimethylamino-2-(4-methylphenylmethyl)-1-(3,4-dimethoxyphenyl)-1-butanone
2-dimethylamino-2-(4-methylphenylmethyl)-1-(4-morpholinophenyl)-1-butanone
2-benzyl-2-dimethylamino-1-(4-morpholinophenyl)-1-butanone
2-benzyl-2-dimethylamino-1-(4-morpholinophenyl)-1-pentanone
2-benzyl-2-dimethylamino-1-(4-dimethylaminophenyl)-1-butanone
2-allyl-2-dimethylamino-1-(4-morpholinophenyl)-pent-4-en-1-one
2-allyl-1-(4-morpholinophenyl)-2-morpholino-pent-4-en-1-one.

Examples of $\alpha$-hydroxycycloalkyl phenyl ketones are:
$\alpha$-hydroxycyclohexyl phenyl ketone
$\alpha$-hydroxycyclopentyl phenyl ketone The photoinitiator mixture (b)+(c) can be added in amounts of 0.5-20, preferably 1 to 10%, by weight, relative to component (a).

The weight ratio of components (b):(c) can be from 1:1 to 30:1, preferably 5:1 to 15:1.

The choice of solvent and the concentration depend principally on the nature of the composition and on the coating process. The composition is applied uniformly to a substrate by known coating processes, for example by dipping, knife coating, curtain coating, electrophoresis, brushing, spraying or reverse-roll coating. The amount applied (coating thickness) and the nature of the substrate (coating base) depend on the desired area of application. The coating bases used are: for photographic information recording, for example films made from polyester or cellulose acetate or plastic-coated papers; for offset printing plates, especially treated aluminium; and for the production of printed circuits, copper-laminated laminates. The coating thicknesses for photographic materials and offset printing plates are generally about 0.5 to about 10 $\mu$m, for printed circuits, generally 1 to about 100 $\mu$m. If solvents are also used, they are removed after coating.

The titanocenes according to the invention may also be used as photoinitiators in photocurable compositions for dental applications. They give, with short irradiation times, materials of high strength and low degree of residual unsaturated components. By irradiating dental compositions based on olefinically unsaturated resins, inorganic fillers and titanocene photoinitiators, hardening depths of several millimeters can be achieved within a few seconds using commercial light sources for dental applications. Examples of compositions for dental materials which can be cured using compounds according to the invention, as well as further details on binders, fillers, further additives and application methods, are given, for example, in EP-A-334,338 and DE-A-3,801,511.

Photocurable compositions as are used for various purposes usually contain a number of other additives in addition to the photopolymerizable compounds and photoinitiators. Thus, it is frequently customary to add thermal inhibitors, which are intended to protect against premature polymerization, particularly during preparation of the compositions by mixing the components. To this end, hydroquinone, hydroquinone derivatives, p-methoxyphenol, β-naphthols or sterically hindered phenols, for example 2,6-di(tert-butyl)-p-cresol, are used for example. Furthermore, small amounts of UV absorbers may be added, for example those of the benzotriazole, benzophenone or oxalanilide type. It is also possible to add light screens of the sterically hindered amine type (HALS).

In order to increase the stability on storage in the dark, copper compounds, such as copper naphthenate, stearate or octanoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, may be added.

In order to exclude the inhibiting effect of atmospheric oxygen, paraffin or similar waxy substances are frequently added to photocurable mixtures. Due to low solubility in the polymer, these float at the beginning of the polymerization and form a transparent surface layer which prevents ingress of air.

Further customary additives are photosensitizers which absorb in certain wavelengths and pass the absorbed energy to the initiators or themselves function as an additional initiator. Examples of these are, in particular, thioxanthone, anthracene, anthraquinone and coumarine derivatives.

Further customary additives are accelerators of the amine type, which are particularly important in pigmented preparations since they act as chain-transfer agents. Examples of these are N-methyldiethanolamine, triethylamine, ethyl p-dimethylaminobenzoate or Michler's ketone. The action of the amines can be reinforced by adding aromatic ketones of the benzophenone type. Further customary accelerators are 1,3,4-thiadiazole derivatives, for example 2-mercapto-5-methylthio-1,3,4-thiadiazole.

Examples of further customary additives are fillers, pigments, dyes, adhesives, wetting agents and flow-control agents.

Photocuring is extremely important for printing inks, since the drying time of the binder is a crucial factor for the production rate of graphic products and should be in the order of fractions of seconds. UV-curable printing inks are particularly important for screen printing.

The photocurable compositions according to the invention are also highly suitable for the production of printing plates, in particular flexographic printing plates. Here, for example, mixtures of soluble, linear polyamides or of styrene-butadiene rubber with photopolymerizable monomers, for example acrylamides or acrylates, and a photoinitiator are used. Films and plates made from these systems are exposed over the negative (or positive) of the print master, and the non-cured areas are subsequently eluted using a solvent.

A further area of application for photocuring is metal coating, for example in the painting of metal sheeting for tubes, cans or bottle caps, and the photocuring of plastic coatings, for example of PVC-based floor coverings or wall coverings.

Examples of the photocuring of paper coatings are the clear coating of labels, record sleeves or book covers.

The use of the photocurable compositions is also important for imaging processes and for optical production of information carriers. Here, the coating (wet or dry) applied to the backing is irradiated with shortwave light through a photomask, and the unexposed areas of the coating are removed by treatment with a solvent (=developer). The exposed areas are crosslinked and polymeric and are thus insoluble and remain on the backing. When stained appropriately, visible images are produced. If the backing is a metallized layer, the metal can be removed at the unexposed areas by etching after exposure and development or thickened by electroplating. In this way, printed circuits and photoresists can be produced.

Light sources having a high proportion of shortwave light are suitable for the exposure. Today, suitable technical equipment and various types of lamps are available for this purpose. Examples are carbon arc lamps, xenon arc lamps, mercury vapour lamps, metal halogen lamps, fluorescent lamps, argon lamps or photographic floodlamps. Recently, laser light sources have also been used. These have the advantage that photomasks are not necessary; the controlled laser beam writes directly on the photocurable coating.

The examples below describe the preparation of the intermediates and of the titanocenes and their use as photoinitiators.

A) PREPARATION OF THE INTERMEDIATES

Example 1

2,4-Difluorobenzylamine 13.9 g (0.10 mol) of 2,4-difluorobenzonitrile are dissolved in 100 ml of ethanol and hydrogenated in a pressurized reactor at 75°–80° C. using hydrogen gas after 1.4 g of Raney nickel in ethanol has been added and after 17 g (1.0 mol) of ammonia gas have been injected. The take-up of hydrogen is complete after about 2 hours. The reaction mixture is cooled, decompressed and filtered and then freed from solvent in a vacuum rotary evaporator. The resultant oil is subjected to fractional distillation at 70°–75° C. in vacuo (19 mbar). 9.5 g (66% of theory) of a colourless liquid are obtained.

| Analysis: $C_7H_7F_2N$ (143.14) | | | | |
|---|---|---|---|---|
| | C | H | F | N |
| calc.: | 58.74 | 4.93 | 26.55 | 9.79% |
| found: | 58.8 | 5.0 | 26.1 | 9.8% |

Example 2

1-[(2,4-Difluorophenyl)methyl]-1H-pyrrole 8.6 g (0.060 mol) of 2,4-difluorobenzylamine are heated in an autoclave with 8 g (0.060 mol) of 2,5-dimethoxytetrahydrofuran for 2 hours at 250° C. The reaction mixture is cooled and then purified by vacuum distillation. 9.2 g (79% of theory) of a colourless oil which boils at 110°–114° C. at 16 mbar are obtained.

| Analysis: $C_{11}H_9F_2N$ (193.20) | | | | |
|---|---|---|---|---|
| | C | H | F | N |
| calc.: | 68.39 | 4.70 | 19.67 | 7.25% |
| found: | 69.1 | 4.9 | 19.2 | 6.9% |

Example 3

1-[(2,4-Difluorophenyl)methyl]-2,5-dimethyl-1H-pyrrole 42.9 g (0.30 mol) of 2,4-difluorobenzylamine are dissolved in 300 ml of ethanol. 5 drops of concentrated hydrochloric acid (36%) are added to this solution. 36.0 g (0.315 mol) of acetonylacetone are then added dropwise, and the mixture is warmed to reflux. The reaction is complete (GC check) after refluxing for 4.5 hours at about 80° C. The brown solution is cooled to $-30°$ C. and the crystals which have precipitated are filtered off and dried. 56.2 g (85% of theory) of white crystals which melt at 41°-42° C. are obtained.

| Analysis: $C_{13}H_{13}F_2N$ (221.25) | | | |
|---|---|---|---|
| | C | H | F | N |
| calc.: | 70.57 | 5.92 | 17.17 | 6.33% |
| found: | 70.3 | 6.1 | 17.0 | 6.2% |

Example 4

1-[(2,4-Difluorophenyl)methyl]-2,2,5,5-tetramethyl-1,2,5-azadisilolidine 107.6 g (0.05 mol) of 1,2-bis(chlorodimethylsilyl)ethane are introduced into 200 ml of dichloromethane. A solution of 71.6 g (0.50 mol) of 2,4-difluorobenzylamine and 101.2 g (1.0 mol) of triethylamine in 300 ml of dichloromethane are added dropwise at room temperature over the course of 2.5 hours, to give a white suspension. The end of the reaction is checked by gas chromatography. 400 ml of 10% sodium dihydrogen phosphate solution are then added in order to dissolve the precipitated triethylammonium chloride. The organic phase is separated off, dried using magnesium sulfate, filtered and evaporated on a vacuum rotary evaporator. The turbid oil is taken up in 300 ml of petroleum ether, clarified and re-evaporated. 124.7 g of a colourless liquid which is purified by fractional distillation at 125°-127° C. and 15 mbar are obtained. 85.3 g (60% or theory) of pure product are obtained.

| Analysis: $C_{13}H_{21}F_2NSi_2$ (285.48) | | | | |
|---|---|---|---|---|
| | C | H | N | F | Si |
| calc.: | 54.69 | 7.41 | 4.91 | 13.31 | 19.67% |
| found: | 54.5 | 7.5 | 4.9 | 13.1 | 19.8% |

Example 5

Ethyl 3-(2,4-difluorophenyl)-2-propenoate 51.6 g (0.40 mol) or 2,4-difluoroaniline are dissolved in 240 ml of glacial acetic acid. 45 ml (0.80 mol) of concentrated sulfuric acid are added slowly with cooling. The white suspension is diazotized at 12°-15° C. using a solution of 28.0 g (0.406 mol) of sodium nitrite in 70 ml of water. 1.2 g (0.0044 mol) of palladium bis(1,5-diphenyl-1,4-pentadien-3-one) (lit.: M. F. Rettig et al., Inorg. Synth. 17 (1977), 134) are added to the resultant yellow solution at 45° C. 40.5 g (0.405 mol) of ethyl acrylate are then added dropwise. The reaction is slightly exothermic, and the temperature slowly rises to about 60° C. The reaction mixture is stirred overnight with falling temperature and then poured into about 600 ml of ice-water. The waxy precipitate is extracted with 500 ml of diethyl ether. The ether phase is separated off, washed several times with ice-water and then dried using sodium sulfate. The ether is removed by distillation on a vacuum rotary evaporator. 51.2 g (60% of theory) of a waxy crystalline product which, after recrystallization from petroleum ether, melts at 40°-40.5° C. are obtained.

| Analysis: $C_{11}H_{10}F_2O_2$ (212.20) | | | |
|---|---|---|---|
| | C | H | F |
| calc.: | 62.26 | 4.75 | 17.91% |
| found: | 62.2 | 4.8 | 17.6% |

Example 6

Ethyl 3-(2,4-difluorophenyl)propanoate 42.4 g (0.20 mol) of ethyl 3-(2,4-difluorophenyl)-2-propenoate are dissolved in 400 ml of ethanol, 4 g of Raney nickel in ethanol are added, and the mixture is hydrogenated at 20°-25° C. using hydrogen gas. When the theoretical amount of hydrogen has been taken up, the solution is filtered and evaporated on a vacuum rotary evaporator. 41.4 g of a pale brown oil which is subjected to fractional distillation at 120° C. in vacuo (20 mbar) are obtained. 33 g (77% of theory) of a colourless oil are obtained.

| Analysis: $C_{11}H_{12}F_2O_2$ (214.21) | | | |
|---|---|---|---|
| | C | H | F |
| calc.: | 61.68 | 5.65 | 17.74% |
| found: | 61.7 | 5.8 | 17.7% |

Example 7

3-(2,4-Difluorophenyl)propanoic acid 33 g (0.154 mol) of ethyl 3-(2,4-difluorophenyl)propanoate are suspended in 250 ml of water. 60 ml of 10N sodium hydroxide solution and 30 ml of 40% tetrabutylammonium hydroxide solution are then added. The mixture is stirred vigorously and warmed. Everything has dissolved at about 50° C. The mixture is warmed further to 80° C. and then cooled to 5° C. On dropwise addition of 80 ml of concentrated hydrochloric acid, white crystals precipitate, which are filtered off and washed with ice-water. After drying in vacuo, 28.1 g (98% of theory) of white crystals of melting point 107°-108° C., which does not change even after recrystallization from 50% ethanol, are obtained.

| Analysis: $C_9H_8F_2O_2$ (186.16) | | | |
|---|---|---|---|
| | C | H | F |
| calc.: | 58.07 | 4.33 | 20.41% |
| found: | 57.8 | 4.4 | 20.4% |

Example 8

3-(2,4-Difluorophenyl)propanamide 27.9 g (0.15 mol) of 3-(2,4-difluorophenyl)propanoic acid are mixed in a sulfation flask with 50 ml (0.69 mol) of thionyl chloride and 0.5 ml of dimethylformamide, and the mixture is stirred at room temperature for one hour, at 50° C. for one hour and under reflux for half an hour. The excess thionyl chloride is then removed by distillation in vacuo. The orange-brown oily residue is dissolved in toluene and then cooled to −15° C. At this temperature, 7.0 g (0.41 mol) of ammonia gas are passed in over about one hour. The temperature is then allowed to rise to room temperature. The partially crystalline reaction mixture is then poured into 500 ml of ice-water. The residue is filtered, washed with a little toluene and dried in vacuo. 21.7 (78% of theory) of white crystals of melting point 107°–108° C. are obtained. After recrystallization from water, the product melts at 109°–110° C.

| Analysis: $C_9H_9F_2NO$ (185.17) | | | | |
|---|---|---|---|---|
| | C | H | F | N |
| calc.: | 58.38 | 4.90 | 20.52 | 7.56% |
| found: | 58.0 | 4.9 | 20.5 | 7.7% |

Example 9

2-(2,4-Difluorophenyl)ethylamine 37.2 g (0.20 mol) of 3-(2,4-difluorophenyl)propanamide are slowly introduced at room temperature into the solution of 38.8 g (0.24 mol) of bromine in 750 ml of 2N sodium hydroxide solution. The reaction mixture is then stirred for a further hour and subsequently subjected to steam distillation. The distillate is extracted with diethyl ether. The ether solution is dried using sodium sulfate, filtered and evaporated in vacuo. 23.7 g of a slightly yellowish oil are obtained. The latter is subjected to fractional distillation at 84°–87° C. in vacuo (21 mbar). 20.3 g (64% of theory) of a colourless oil are obtained.

| Analysis: $C_8H_9F_2N$ (157.16) | | | | |
|---|---|---|---|---|
| | C | H | F | N |
| calc.: | 61.14 | 5.77 | 24.17 | 8.91% |
| found: | 60.9 | 5.7 | 24.3 | 9.0% |

Example 10

1-[2-(2,4-Difluorophenyl)ethyl]-1H-pyrrole 15.7 g (0.10 mol) of 2-(2,4-trifluorophenyl)ethylamine are heated for 2 hours at 260° C. in an autoclave with 13.2 g (0.10 mol) of 2,5-dimethoxytetrahydrofuran. The reaction mixture is cooled and then purified by vacuum distillation. 17.2 g (83% of theory) of a colourless oil which boils at 90°–93° C. at 0.033 mbar are obtained.

| Analysis: $C_{12}H_{11}F_2N$ (207.23) | | | | |
|---|---|---|---|---|
| | C | H | F | N |
| calc.: | 69.56 | 5.35 | 18.34 | 6.76% |
| found: | 69.8 | 5.3 | 18.2 | 7.1% |

Example 11

3-(2,4-Difluorophenyl)propionitrile 74.0 g (0.40 mol) of 3-(2,4-difluorophenyl)propanamide are mixed with 124 g (0.87 mol) of phosphorus pentoxide, and the mixture is heated to 200° C. in an oil bath in a flask fitted with falling condenser. The resultant liquid is distilled off by applying a vacuum of about 67 mbar. 48.5 g of a colourless oil, which is subjected to fractional distillation at 120°–124° C. in vacuo (19 mbar), are obtained. 46.5 g (70% of theory) of the expected product are obtained.

| Analysis: $C_9H_7F_2N$ (167.16) | | | | |
|---|---|---|---|---|
| | C | H | F | N |
| calc.: | 64.67 | 4.22 | 22.73 | 8.38% |
| found: | 64.7 | 4.2 | 22.8 | 8.5% |

Example 12

3-(2,4-Difluorophenyl)propylamine 33.4 g (0.20 mol) of 3-(2,4-difluorophenyl)propionitrile are dissolved in 200 ml of ethanol and, after 2.8 g of Raney nickel in ethanol have been added and after 34 g (2.0 mol) of ammonia gas have been injected, are hydrogenated using hydrogen gas in a pressurized reactor at 75°–80° C. The take-up of hydrogen is complete after about 3 hours. The reaction mixture is cooled, decompressed and filtered and then freed from solvent on a vacuum rotary evaporator. The resultant oil is subjected to fractional distillation at 89°–90° C. in vacuo (13 mbar). 26.0 g (76% of theory) of a colourless oil are obtained.

| Analysis: $C_9H_{11}F_2N$ (171.19) | | | | |
|---|---|---|---|---|
| | C | H | F | N |
| calc.: | 63.15 | 6.48 | 22.20 | 8.18% |
| found: | 63.6 | 6.5 | 22.3 | 8.3% |

Example 13

1-[3-(2,4-Difluorophenyl)propyl]-1H-pyrrole 17.1 g (0.10 mol) of 3-(2,4-difluorophenyl)propylamine are heated at 260° C. for 2 hours in an autoclave with 13.2 g (0.10 mol) of 2,4-dimethoxytetrahydrofuran. The reaction mixture is cooled and then purified by vacuum distillation. 10.6 g (48% of theory) of a colourless oil which boils at 80° C. and 0.2 mbar or 146°–147° C. and 15 mbar are obtained.

| Analysis: $C_{13}H_{13}F_2N$ (221.26) | | | | |
|---|---|---|---|---|
| | C | H | F | N |
| calc.: | 70.58 | 5.92 | 17.17 | 6.33% |
| found: | 70.7 | 6.0 | 17.4 | 6.5% |

Example 14

N-Benzylidene-2,4-difluorobenzylamine 50.2 g (0.35 mol) of 2,4-difluorobenzylamine and 37.1 g (0.35 mol) of benzaldehyde are dissolved in 140 ml of toluene and heated to reflux. The water produced is separated off using a water separator. The reaction is complete (GC check) after two hours. The solution is evaporated on a vacuum rotary evaporator. 78.9 g (97% of theory) of a slightly yellow liquid are obtained.

| Analysis: $C_{14}H_{11}F_2N$ (231.25) | | | |
|---|---|---|---|
| | C | H | N |
| calc.: | 72.72 | 4.79 | 6.06% |
| found: | 72.69 | 6.0 | 6.01% |

Example 15

3-Chloro-2,2-dimethyl-N-[(2,4-difluorophenyl)methyl]-propanamide 28.6 g (0.20 mol) of 2,4-difluorobenzylamine and 19.0 g (0.24 mol) of pyridine are dissolved in 100 ml of toluene. 34.1 g (0.22 mol) of chloropivaloyl chloride are added dropwise to this solution at 20°–25° C. over the course of 15 minutes with ice-bath cooling. A suspension forms and is stirred for a further 3 hours at room temperature until the reaction is complete (GC check). For work-up, the pH is adjusted to between 1 and 2 using 50 ml of 2N hydrochloric acid. The white emulsion produced is extracted three times with 100 ml of toluene. The extract is washed with 100 ml of water, dried using magnesium sulfate and evaporated on a vacuum rotary evaporator. 49.2 g (94% of theory) of a yellow oil are obtained.

| | Analysis: $C_{12}H_{14}F_2ClNO$ (261.70) | | | |
|---|---|---|---|---|
| | C | H | N | Cl |
| calc.: | 55.08 | 5.39 | 5.35 | 13.55% |
| found: | 54.87 | 5.37 | 4.92 | 13.94% |

Example 16

3,3-Dimethyl-1-[(2,4-difluorophenyl)methyl]-2-azetidinone 49.7 g (0.19 mol) of 3-chloro-2,2-dimethyl-N-[(2,4-difluorophenyl)methyl]propanamide and 78.8 g (0.57 mol) of potassium carbonate are suspended in 200 ml of methyl ethyl ketone, and the suspension is warmed and stirred at 75° C. for 24 hours. When the reaction is complete (GC check), the mixture is filtered, and the filtrate is evaporated on a vacuum rotary evaporator. 40.9 g (95% of theory) of a yellow oil are obtained.

| | Analysis: $C_{12}H_{13}F_2NO$ (225.24) | | |
|---|---|---|---|
| | C | H | N |
| calc.: | 63.99 | 5.82 | 6.22% |
| found: | 63.38 | 5.94 | 5.91% |

Example 17

N-Hexyl-2,4-difluorobenzylamine 71.6 g (0.50 mol) of 2,4-difluorobenzylamine, 100.2 g (1.0 mol) of caproaldehyde, 1.0 g of acetic acid, 10 g of Raney nickel in ethanol and 500 ml of tetrahydrofuran are introduced into a 1 l autoclave. This mixture is heated to 100° C. and hydrogenated with stirring and under a pressure of 100 bar. After 13 hours, the take-up of hydrogen is 142% of theory. The black suspension is filtered, and the filtrate is evaporated on a rotary evaporator and subsequently distilled at 77° C. and 2 mbar. 33.1 g of a colourless liquid are obtained.

| | Analysis: $C_{13}H_{19}F_2N$ (227.30) | | |
|---|---|---|---|
| | C | H | N |
| calc.: | 68.70 | 8.43 | 6.16% |
| found: | 68.31 | 8.40 | 5.63% |

Example 18

N-[(2,4-Difluorophenyl)methyl]-N-hexyl-2,2-dimethyl-pentanamide 22.7 g (0.10 mol) of N-hexyl-2,4-difluorobenzylamine and 24.3 g (0.24 mol) of triethylamine are dissolved in 150 ml of diethyl ether. A solution of 17.8 g (0.12 mol) of 2,2-dimethylpentanoyl chloride in 50 ml of diethyl ether is added dropwise at room temperature over the course of 30 minutes. The mixture is stirred for a further 18 hours at room temperature until the reaction is complete (GC check). For work-up, the resultant suspension is adjusted to pH 7 using 70 ml of 2N hydrochloric acid. Everything dissolves, and two phases form, which are separated. The organic phase is washed with 50 ml of water, dried using magnesium sulfate, filtered and evaporated on a vacuum rotary evaporator. 37.8 g of a pale yellow liquid, which is subjected to fractional distillation, are obtained. 21.4 g (63% of theory) of a colourless oil which boils at 126°–127° C. and 0.4 mbar are obtained.

| | Analysis: $C_{20}H_{31}F_2NO$ (339.47) | | |
|---|---|---|---|
| | C | H | N |
| calc.: | 70.76 | 9.20 | 4.13% |
| found: | 70.60 | 9.39 | 4.20% |

B) PREPARATION OF THE TITANOCENES

Example 19

Bis(cyclopentadienyl)bis[2,6-difluoro-3-(2-(1H-pyrr-1-yl-ethyl)phenyl]titanium 2.5 g (0.010 mol) of bis(cyclopentadienyl)titanium dichloride and 4.6 g (0.022 mol) of 1-[2-(2,4-difluorophenyl)ethyl]-1H-pyrrole in 30 ml of freshly distilled, absolute tetrahydrofuran are introduced into a 100 ml Schlenk tube under argon as protective gas and cooled to −20° C. A solution of lithium diisopropylamide, prepared in a 50 ml Schlenk tube under argon from 3.1 ml (0.022 mol) of diisopropylamine in 15 ml of absolute tetrahydrofuran and 13.7 ml (0.022 mol) of 1.6 molar butyllithium solution in hexane at −10° to 0° C. is added dropwise to this red suspension with stirring at −20° C. over the course of 30 minutes. The brown-red solution is stirred for a further 2 hours at −20° C. After this time, the reaction is complete according to a check by thin-layer chromatography. The solution is then added to a mixture of 100 ml of ethyl acetate, 100 ml of water and 1.3 g (0.022 mol) of acetic acid, and the mixture is stirred. The orange suspension is filtered through Hyflo. The two phases of the filtrate are separated from one another. The organic phase is dried using magnesium sulfate and evaporated in a vacuum rotary evaporator at 20 mbar and a water-bath temperature of 50° C. 7.9 g of a dark-red oil, which is purified by flash chromatography using hexane/ethyl acetate (9:1) as solvent, are obtained. 3.3 g of an orange-red glassy resin are obtained.

| | Analysis: $C_{34}H_{30}F_4N_2Ti$ (590.52) | | |
|---|---|---|---|
| | C | H | N |
| calc.: | 69.16 | 5.12 | 4.74% |
| found: | 68.5 | 5.2 | 4.6% |

Example 20

Bis(cyclopentadienyl)bis[2,6-difluoro-3-(3-(1H-pyrr-1-yl)propyl)phenyl]titanium

Analogously to Example 19, 2.5 g (0.010 mol) of bis(cyclopentadienyl)titanium dichloride and 4.9 g (0.022 mol) of 1-[3-(2,4-difluorophenyl)propyl]-1H-pyrrole are reacted with 0.022 mol of lithium diisopropylamide solution. The brown-orange oil is purified by means of flash chromatography using hexane/ethyl acetate (9:1) as solvent. 2.3 g of an orange glassy resin are obtained.

| Analysis: $C_{36}H_{34}F_4N_2Ti$ (618.57) | | | |
|---|---|---|---|
| | C | H | N |
| calc.: | 69.90 | 5.54 | 4.54% |
| found: | 69.4 | 5.6 | 4.3% |

Example 21

Bis(cyclopentadienyl)bis[2,6-difluoro-3-((1H-pyrr-1-yl)methyl)phenyl]titanium

Analogously to Example 19, 2.5 g (0.010 mol) of bis(cyclopentadienyl)titanium dichloride and 4.25 g (0.022 mol) of 1-[(2,4-difluorophenyl)methyl]-1H-pyrrole are reacted with 0.022 mol of lithium diisopropylamide solution. 3.1 g of orange crystals melting point 192°–194° C. are obtained.

| Analysis: $C_{32}H_{26}F_4N_2Ti$ (562.46) | | | |
|---|---|---|---|
| | C | H | N |
| calc.: | 68.33 | 4.66 | 4.98% |
| found: | 68.4 | 4.7 | 5.0% |

Example 22

Bis(methylcyclopentadienyl)bis[2,6-difluoro-3-((1H-pyrr-1-yl)-methyl)phenyl]titanium Analogously to Example 19, 2.77 g (0.010 mol) of bis(methylcyclopentadienyl)titanium dichloride and 4.25 g (0.022 mol) of 1-[2,4-difluorophenyl)methyl]-1H-pyrrole are reacted with 0.022 mol of lithium diisopropylamide solution. 7.2 g of a dark-red oil, from which 3.6 g of orange crystals which melt at 112°–115° C. are obtained by recrystallization from ethanol, are obtained.

| Analysis: $C_{34}H_{30}F_4N_2Ti$ (590.52) | | | |
|---|---|---|---|
| | C | H | N |
| calc.: | 69.16 | 5.12 | 4.74% |
| found: | 69.1 | 5.2 | 4.6% |

Example 23

Bis(cyclopentadienyl)bis[2,6-difluoro-3-((2,5-dimethyl-1H-pyrr-1-yl)methyl)phenyl]titanium Analogously to Example 19, 2.5 g (0.010 mol) of bis(cyclopentadienyl)titanium dichloride and 4.9 g (0.022 mol) of 2,5-dimethyl-1-[2,4-difluorophenyl)methyl]-1H-pyrrole are reacted with 0.022 mol of lithium diisopropylamide solution. 7.1 g of an orange oil, which is purified by flash chromatography using hexane/ethyl acetate (3:1) as eluent, are obtained. 2.5 g of an orange, glassy resin are obtained.

| Analysis: $C_{36}H_{34}F_4N_2Ti$ (618.57) | | | |
|---|---|---|---|
| | C | H | N |
| calc.: | 69.90 | 5.54 | 4.53% |
| found: | 69.6 | 5.9 | 4.2% |

Example 24

Bis(cyclopentadienyl)bis[2,6-difluoro-3-(N-hexyl-(2,2-dimethylpentanoyl)amino)methyl)phenyl]titanium Analogously to Example 19, 2.5 g (0.010 mol) of bis(cyclopentadienyl)titanium dichloride and 7.5 g (0.022 mol) of N-[2,4-difluorophenyl)methyl]-N-hexyl-2,2-dimethylpentanamide are reacted with 0.022 mol of lithium diisopropylamide solution. The orange oil is purified by flash chromatography using hexane/ethyl acetate (9:1) as solvent. 1.8 g of an orange resin are obtained.

| Analysis: $C_{50}H_{70}F_4N_2O_2Ti$ (855.00) | | | |
|---|---|---|---|
| | C | H | N |
| calc.: | 70.24 | 8.25 | 3.28% |
| found: | 69.76 | 8.44 | 3.32% |

C) USE EXAMPLES

Example 25

Photocuring of an acrylate mixture

A photocurable composition is prepared by mixing the following components:

| | Solids content |
|---|---|
| 150.30 g of Scripset 540[1] (30% solution in acetone) | 45.1 g |
| 48.30 g of trimethylolpropane triacrylate | 48.3 g |
| 6.60 g of polyethylene glycol diacrylate | 6.6 g |
| 0.08 g of crystal violet | |
| 205.28 g | 100.0 g |

[1] Polystyrene-maleic anhydride copolymer (Monsanto)

Portions of this composition are in each case mixed with 0.3% (relative to the solids content) of photoinitiator. All operations are carried out under a red light or yellow light.

The samples mixed with initiator are applied in a thickness of 150 μm to a 200 μm aluminium foil (10×15 cm). The solvent is removed by warming at 60° C. for 15 minutes in a circulation oven. A 76 μm thick polyester film is placed on the liquid coating, and this is covered by a standardized test negative with 21 steps of different optical density (Stouffer wedge). This is covered by a second polyester film, and the resultant laminate is fixed onto a metal plate. The sample is exposed with a 5 kW metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 120 seconds using developer A and subsequently dried at 60° for 15 minutes in a circulation oven. The sensitivity of the initiator system used in characterized by indicating the final wedge step imaged without adhesion. The higher the number of steps, the more sensitive the system. An increase by two steps indicates an approximate doubling of the curing rate. The results are given in Table 1. Developer A contains 15 g of sodium metasilicate.$H_2O$; 0.16 g of KOH; 3 g of polyethylene glycol 6000; 0.5 g of levulinic acid and 1000 g of deionized water.

TABLE 1

| Titanocene Example | Number of imaged steps after exposure for | | |
|---|---|---|---|
| | 10s | 20s | 40s |
| 19 | 11 | 14 | 17 |
| 20 | 10 | 14 | 17 |
| 21 | 11 | 13 | 16 |
| 22 | 8 | 11 | 13 |
| 23 | 8 | 10 | 12 |
| 24 | 8 | 11 | 12 |

Example 26

Photocuring of a monomer/polymer mixture

A photocurable composition is prepared by mixing the following components:

| | |
|---|---|
| 37.64 g | of Sartomer SR 444 (pentaerythritol triacrylate) (Sartomer Company, Westchester) |
| 10.76 g | of Cymel 301 (hexamethoxymethylmelamine) (Cyanamid) |
| 47.30 g | of Carboset 525 (thermoplastic polyacrylate containing carboxyl groups/B.F. Goodrich) |
| 4.30 g | polyvinylpyrrolidone PVP (GAF) |
| 100.00 g | of the above mixture |
| 0.50 g | of Irgalit Green GLN |
| 319.00 g | of methylene chloride |
| 30.00 g | of methanol |
| 450.00 g | |

Portions of this composition are in each case mixed with 0.3% (relative to the solids content) of the titanocenes indicated in the table below. All operations are carried out under a red light or yellow light.

The samples mixed with initiator are applied in a thickness of 200 μm to a 200 μm aluminium foil (10×15 cm). The solvent is removed by warming at 60° C. for 15 minutes in a circulation oven. A 76 μm thick polyester film is placed on the liquid coating, and this is covered by a standardized test negative with 21 steps of different optical density (Stouffer wedge). This is covered by a second polyester film, and the resultant laminate is fixed onto a metal plate. The sample is exposed with a 5 kW metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 240 seconds using developer A and subsequently dried at 60° for 15 minutes in a circulation oven. The sensitivity of the initiator system used is characterized by indicating the final wedge step imaged without adhesion. The higher the number of steps, the more sensitive the system. An increase by two steps indicates an approximate doubling of the curing rate. The results are given in Table 2.

TABLE 2

| Titanocene Example | Number of imaged steps after exposure for | | |
|---|---|---|---|
| | 10s | 20s | 40s |
| 19 | 12 | 14 | 17 |
| 20 | 11 | 14 | 17 |
| 21 | 12 | 15 | 18 |
| 22 | 9 | 11 | 14 |

TABLE 2-continued

| Titanocene Example | Number of imaged steps after exposure for | | |
|---|---|---|---|
| | 10s | 20s | 40s |
| 23 | 11 | 13 | 16 |

What is claimed is:
1. A titanocene of the formula I

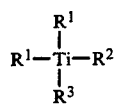

in which both the $R^1$ radicals, independently of one another, are cyclopentadienyl⊖, indenyl⊖ or 4,5,6,7-tetrahydroindenyl⊖, each of which is unsubstituted, monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{16}$aryl, $C_7$-$C_{16}$aralkyl, —Si($R^4$)$_3$, —Ge($R^4$)$_3$, cyano or halogen, and $R^4$ is $C_1$-$C_{12}$alkyl, $C_5$-$C_{12}$cycloalkyl, $C_6$-$C_{10}$aryl or $C_7$-$C_{16}$aralkyl, $R^2$ is a 6-membered carbocyclic or 5- or 6-membered heterocyclic aromatic ring which is substituted by fluorine atoms at least in the two ortho-positions to the titanium-carbon bond, and in which the aromatic ring may contain further substituents, and $R^3$, independently, is as defined for $R^2$, $R^2$ and $R^3$ in the titanocenes being substituted by a radical of the formula II, IIa or IIb

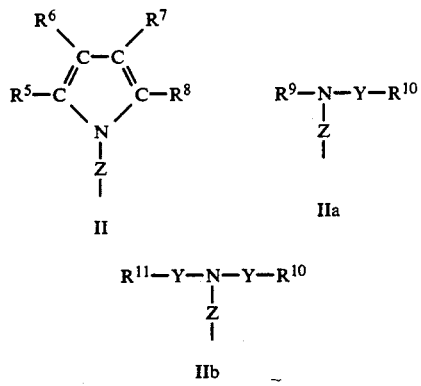

in which $R^5$, $R^6$, $R^7$ and $R^8$, independently of one another, are hydrogen or linear or branched $C_1$-$C_{18}$alkyl, $C_2$-$C_5$alkenyl, $C_7$-$C_9$aralkyl, $C_7$-$C_9$alkaryl, $C_8$-$C_{10}$alkaralkyl, $C_6$-$C_{10}$aryl, 2-furyl, $C_5$-$C_8$cycloalkyl, $C_5$-$C_8$cycloalkenyl, $C_2$-$C_{12}$alkanoyl, $C_2$-$C_{12}$alkoxycarbonyl, —CHO, —Si($R^4$)$_3$ or —Ge($R^4$)$_3$, these radicals being unsubstituted or substituted by $C_2$-$C_8$dialkylamino, bis[2-($C_1$-$C_4$alkoxy)ethyl]amino, morpholino, piperidino, N-methylpiperazino, pyrrolidino, quaternary $C_3$-$C_{10}$trialkylammonium, $C_1$-$C_{12}$alkoxy, ${+OCH_2CH_2)_p}$ O$C_1$-$C_{16}$alkyl, in which p is a number from 1 to 20, 1,3-dioxolan-2-yl, 4-methyl-1,3-dioxolan-2-yl, —OCH$_2$CH$_2$O—, $C_2$-$C_{12}$alkoxycarbonyl, $C_2$-$C_{12}$alkanoyloxy, $C_2$-$C_{12}$alkanoyl, $C_1$-$C_{12}$alkylthio, halogen, cyano or —Si($R^4$)$_3$, or $R^5$ and $R^6$ and/or $R^7$ and $R^8$ or $R^6$ and $R^7$ are each together —(CH$_2$)$_3$—, —(CH$_2$)$_4$—, —CH=CH—CH=CH—, —CH=CH—C($R^{12}$)=CH—, —CH$_2$OCH$_2$— or —CH$_2$N(C$_1$-C$_4$alkyl)CH$_2$—, in which $R^{12}$ is hydroxyl, $C_1$-$C_4$alkoxy or $C_2$-$C_4$alkanoyloxy, Y is a —CO—, —CS—, —COO—, —SO$_2$— or —Si($R^4$)$_2$— group, $R_9$ is hydrogen, linear or branched $C_1$-$C_{20}$alkyl, $C_2$-$C_{20}$alkenyl, $C_3$-$C_8$cycloalkyl, $C_4$-$C_{20}$cycloalkylalkyl, $C_4$-$C_{20}$alkylcycloalkyl, $C_5$-$C_{20}$alkylcycloalkylalkyl, $C_6$-$C_{20}$cycloalkenylalkyl, $C_6$-$C_{14}$aryl, $C_7$-$C_{20}$aralkyl, $C_7$-$C_{20}$alkaryl, $C_8$-$C_{20}$alkaralkyl or $C_3$-$C_{12}$trialkylsilyl, these radicals being unsubstituted or substituted by $C_1$-$C_{18}$alkoxy, $C_1$-$C_{18}$alkylthio, $C_1$-$C_{18}$alkylsulfonyl, $C_6$-$C_{10}$arylsulfonyl, $C_7$-$C_{20}$alkarylsulfonyl, 2-tetrahydrofuranyl or cyano, $R^{10}$ has one of the meanings given for $R^9$ or is $C_1$-$C_2$ohaloalkyl, $C_2$-$C_{20}$alkyl which is interrupted by —CO—, or is $C_1$-$C_{12}$alkyl which is substituted by —COOH or —COOR$^4$, and in the case where Y is —CO—, —CS— or —SO$_2$—, may alternatively be —NR$^{13}$R$^{14}$ in which R$^{13}$ and R$^{14}$, independently of one another, have one of the meanings given for $R^9$, or $R^{13}$ and $R^{14}$ together are $C_3$-$C_7$alkylene which may be interrupted by —O—, —S— or —N(R$^{15}$)—, in which $R^{15}$ is hydrogen, $C_1$-$C_{12}$alkyl, $C_3$-$C_{12}$alkenyl, $C_7$-$C_{12}$aralkyl or $C_2$-$C_{20}$alkanoyl, or $R^9$ and $R^{10}$ together are linear or branched $C_2$-$C_8$alkylene or $C_2$-$C_8$alkylene which is substituted by halogen, $C_1$-$C_4$alkoxy, allyloxy or —NR$^{13}$R$^{14}$, or are a divalent radical of the formula

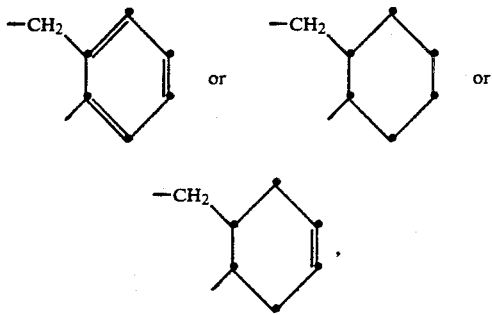

R$^{11}$ has one of the meanings given for R$^{10}$, or R$^{11}$ and R$^{10}$ together are $C_1$-$C_8$alkanediyl, $C_2$-$C_8$alkenediyl, $C_6$-$C_{14}$arenediyl, $C_4$-$C_{12}$cycloalkanediyl, $C_5$-$C_{12}$cycloalkenediyl, $C_6$-$C_{14}$cycloalkadienediyl, $C_7$-$C_{20}$bicycloalkanediyl, $C_7$-$C_{20}$bicycloalkenediyl, or $C_2$-$C_4$alkanediyl which is interrupted by —O—, —S— or —N(R$^{15}$)—, these radicals being unsubstituted or substituted by one or more of the substituents halogen, $C_1$-$C_{10}$alkoxy, $C_1$-$C_{20}$alkyl, $C_3$-$C_{20}$alkenyl or $C_6$-$C_{14}$aryl, and Z is $C_1$-$C_{20}$alkanediyl which is unsubstituted or substituted by —COOR$^4$, —CN or halogen.

2. A titanocene according to claim 1, wherein R$^1$ is cyclopentadienyl$^\ominus$ or methylcyclopentadienyl$^\ominus$.

3. A titanocene according to claim 1, wherein R$^1$ is cyclopentadienyl$^\ominus$.

4. A titanocene according to claim 1, wherein R$^2$ and R$^3$ are identical.

5. A titanocene according to claim 1, wherein R$^2$ and R$^3$ are 2,6-difluorophen-1-yl to which a radical of the formula II, IIa or IIb is bonded, and which may contain a further 1 or 2 identical or different substituents.

6. A titanocene according to claim 5, wherein, in the formula I, both R$^1$ groups are cyclopentadienyl$^\ominus$, and R$^2$ and R$^3$ are radicals of the formula III

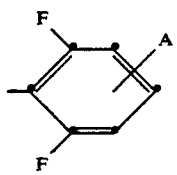 III in which A is a group of the formula II, IIa or IIb.

7. A titanocene according to claim 6, wherein in the formula III, the group A is bonded in the ortho-position to an F atom.

8. A titanocene according to claim 1, wherein R$^2$ and R$^3$ are substituted by a radical of the formula II.

9. A titanocene according to claim 8, wherein R$^5$, R$^6$, R$^7$ and R$^8$, independently of one another, are hydrogen, $C_1$-$C_{12}$alkyl, $C_2$-$C_5$alkenyl, $C_7$-$C_9$phenylalkyl, $C_7$-$C_{10}$alkylphenyl, phenyl, 2-furyl, $C_5$- or $C_6$cycloalkyl, $C_5$-or $C_6$cycloalkenyl, $C_2$-$C_8$alkanoyl, $C_2$-$C_5$alkoxycarbonyl, —CHO or —Si(R$^4$)$_3$, in which R$^4$ is $C_1$-$C_8$alkyl or phenyl, each of which is unsubstituted or substituted by $C_2$-$C_8$dialkylamino, bis(2-methoxyethyl)amino, morpholino, piperidino, $C_1$-$C_{12}$alkoxy, $\pm$(OCH$_2$CH$_2$)$_p$OC$_1$-$C_{12}$alkyl where p = 1-3, 1,3-dioxolan-2-yl, —OCH$_2$CH$_2$O—, $C_2$-$C_8$alkanoyloxy, $C_1$-$C_8$alkoxycarbonyl, halogen, cyano, $C_1$-$C_4$alkylthio or —Si(CH$_3$)$_3$, and Z is unsubstituted $C_1$-$C_8$alkanediyl.

10. A titanocene according to claim 8, wherein R$^5$, R$^6$, R$^7$ and R$^8$, independently of one another, are hydrogen, $C_1$-$C_8$alkyl, $C_2$-$C_4$alkenyl, phenyl, 2-furyl or —Si(R$^4$)$_3$, in which R$^4$ is $C_1$-$C_4$alkyl, each of which is unsubstituted or substituted by $C_2$-$C_8$dialkylamino, morpholino, $C_1$-$C_4$alkoxy, 1,3-dioxolan-2-yl or cyano, and Z is unsubstituted $C_1$-$C_4$alkanediyl.

11. A titanocene according to claim 8, wherein R$^5$, R$^6$, R$^7$ and R$^8$, independently of one another, are hydrogen or $C_1$-$C_4$alkyl.

12. A titanocene according to claim 8, wherein R$^6$ and R$^7$ are hydrogen.

13. A titanocene according to claim 1, wherein R$^2$ and R$^3$ are substituted by a group of the formula IIa, in which Y is —CO—, —COO— or —SO$_2$—, R$^9$ is hydrogen, $C_1$-$C_{12}$alkyl, $C_2$-$C_5$alkenyl, $C_5$-$C_8$cycloalkyl, $C_6$-$C_{18}$cycloalkylalkyl, $C_6$-$C_{18}$alkylcycloalkyl, $C_7$-$C_{18}$alkylcycloalkylalkyl, $C_7$-$C_{16}$aralkyl or $C_8$-$C_{16}$alkaralkyl, each of which is unsubstituted or substituted by $C_1$-$C_{12}$alkoxy or tetrahydrofuryl, R$^{10}$ has one of the meanings given for R$^9$ or is $C_6$-$C_{10}$aryl, $C_6$-$C_{10}$haloaryl, $C_7$-$C_{18}$alkaryl or $C_1$-$C_{12}$haloalkyl, or in the case where Y is —CO— or —SO$_2$— R$^{10}$ is alternatively —NR$^{13}$R$^{14}$, in which R$^{13}$ and R$^{14}$, independently of one another, are hydrogen, $C_1$-$C_{12}$alkyl, phenyl, benzyl or cyclohexyl, or R$^{13}$ and R$^{14}$ together are $C_4$-$C_5$alkylene or 3-oxapentamethylene, or R$^9$ and R$^{10}$ together are $C_2$-$C_8$alkylene, and Z is unsubstituted $C_1$-$C_8$alkanediyl.

14. A titanocene according to claim 13, wherein R$^9$ is hydrogen, $C_1$-$C_{12}$alkyl, cyclohexyl, cyclohexylmethyl, 2-tetrahydrofurylmethyl, $C_2$-$C_8$alkoxyalkyl, allyl or $C_7$-$C_9$aralkyl, R$^{10}$ is $C_1$-$C_{18}$alkyl, $C_1$-$C_4$haloalkyl, cyclohexyl, $C_6$-$C_{10}$aryl, halophenyl or $C_7$-$C_{18}$alkaryl, or R$^9$ and R$^{10}$ together are $C_2$-$C_6$alkylene, Y is —CO—, —COO— or —SO$_2$— or the radical —Y—R$^{10}$ is a —CO—NHR$^{13}$, —CS—NHR$^{13}$, —CO—NR$^{13}$R$^{14}$ or —SO$_2$—NR$^{13}$R$^{14}$ group, in which R$^{13}$ is $C_1$-$C_{12}$alkyl or phenyl, R$^{14}$ is $C_1$-$C_{12}$alkyl, or R$^{13}$ and R$^{14}$ together are $C_4$-$C_5$alkylene or 3-oxapentamethylene, and Z is unsubstituted $C_1$-$C_8$alkanediyl.

15. A titanocene according to claim 14, in which R$^9$ is hydrogen, $C_1$-$C_8$alkyl or $C_7$-$C_9$aralkyl, R$^{10}$ is $C_1$-$C_8$alkyl, trifluoromethyl, phenyl or phenyl which is substituted by halogen or $C_1$-$C_{12}$alkyl, or R$^9$ and R$^{10}$ together are $C_2$-$C_6$alkylene, Y is —CO— or —SO$_2$—, and Z is unsubstituted $C_1$-$C_4$alkanediyl.

16. A titanocene according to claim 1, wherein R$^2$ and R$^3$ are substituted by a group of the formula IIb in which R$^{10}$ and R$^{11}$ together are $C_2$-$C_8$alkanediyl, $C_2$-$C_8$alkenediyl, $C_6$-$C_{14}$arenediyl, cyclohexanediyl or $C_7$-$C_{12}$bicycloalkanediyl, Y is —CO—, and Z is unsubstituted $C_1$-$C_4$alkanediyl.

* * * * *